US011339371B2

(12) United States Patent
Ma

(10) Patent No.: US 11,339,371 B2
(45) Date of Patent: May 24, 2022

(54) METHOD FOR INDUCING PLURIPOTENT STEM CELLS TO DIFFERENTIATE INTO VENTRICULAR MYOCYTES IN VITRO

(71) Applicant: Institute of Biophysics, Chinese Academy of Sciences, Beijing (CN)

(72) Inventor: Yue Ma, Beijing (CN)

(73) Assignee: INSTITUTE OF BIOPHYSICS, CHINESE ACADEMY OF SCIENCES, Beijing (CN)

( * ) Notice: Subject to any disclaimer, the term of this patent is extended or adjusted under 35 U.S.C. 154(b) by 0 days.

(21) Appl. No.: 14/417,101

(22) PCT Filed: Jul. 22, 2013

(86) PCT No.: PCT/CN2013/079811
§ 371 (c)(1),
(2) Date: Aug. 14, 2015

(87) PCT Pub. No.: WO2014/015777
PCT Pub. Date: Jan. 30, 2014

(65) Prior Publication Data
US 2015/0299658 A1  Oct. 22, 2015

(30) Foreign Application Priority Data

Jul. 23, 2012 (CN) .......................... 201210257088.6

(51) Int. Cl.
| | |
|---|---|
| *C12N 5/077* | (2010.01) |
| *A61K 35/34* | (2015.01) |
| *A61K 35/28* | (2015.01) |
| *A61K 35/545* | (2015.01) |

(52) U.S. Cl.
CPC ............ *C12N 5/0657* (2013.01); *A61K 35/28* (2013.01); *A61K 35/34* (2013.01); *A61K 35/545* (2013.01); *C12N 2501/115* (2013.01); *C12N 2501/155* (2013.01); *C12N 2501/16* (2013.01); *C12N 2501/385* (2013.01); *C12N 2501/40* (2013.01); *C12N 2501/415* (2013.01); *C12N 2503/02* (2013.01); *C12N 2506/02* (2013.01); *C12N 2506/45* (2013.01)

(58) Field of Classification Search
CPC ............ C12N 5/0657; C12N 2501/155; C12N 2501/415; A61K 35/34; A61K 35/545
USPC ........................................................ 435/377
See application file for complete search history.

(56) References Cited

U.S. PATENT DOCUMENTS

| | | | |
|---|---|---|---|
| 5,686,102 A | 11/1997 | Gross et al. | |
| 5,736,154 A | 4/1998 | Fuisz | |
| 5,741,511 A | 4/1998 | Cho et al. | |
| 5,886,039 A | 3/1999 | Kock et al. | |
| 5,941,868 A | 8/1999 | Kaplan et al. | |
| 6,197,801 B1 | 3/2001 | Lin | |
| 6,258,374 B1 | 7/2001 | Friess et al. | |
| 6,800,480 B1 | 10/2004 | Bodnar et al. | |
| 7,449,334 B2 | 11/2008 | Thomson et al. | |
| 7,452,718 B2 | 11/2008 | Gold et al. | |
| 7,727,762 B2 | 6/2010 | Fukuda et al. | |
| 8,252,583 B2 | 8/2012 | Fukuda et al. | |
| 8,951,798 B2 | 2/2015 | Palecek et al. | |
| 9,273,286 B2* | 3/2016 | Ma ........................ | C12N 5/0657 |
| 10,590,386 B2 | 3/2020 | Ma | |
| 2004/0106096 A1 | 6/2004 | Thomson et al. | |
| 2005/0214939 A1* | 9/2005 | Gold ..................... | C12N 5/0657 435/366 |
| 2008/0038820 A1* | 2/2008 | Rudy-Reil ............ | C12N 5/0657 435/377 |

(Continued)

FOREIGN PATENT DOCUMENTS

| | | |
|---|---|---|
| AU | 2015230768 B2 | 12/2017 |
| CA | 2395950 A1 | 7/2001 |

(Continued)

OTHER PUBLICATIONS

Han et al., "Pretreatment of Mesenchymal Stem Cells With a Combination of Growth Factors Enhances Gap Junction Formation, Cytoprotective Effect On Cardiomyocytes, and Therapeutic Efficacy for Myocardial Infarction", Journal of the American College of Cardiology, 2008, vol. 51, No. 9, pp. 933-943.*
Hartung et al., "Toxicology for the twenty-first century," Nature (2009) 460(7252):208-212.
He et al., "Human embryonic stem cells develop into multiple types of cardiac myocytes: action potential characterization," Circ Res (2003) 93(1):32-39.
International Search Report and Written Opinion for PCT/CN2013/079811, dated Oct. 24, 2013, 30 pages.
Kattman et al., "Stage-specific optimization of activin/nodal and BMP signaling promotes cardiac differentiation of mouse and human pluripotent stem cell lines," Cell Stem Cell (2011) 8(2):228-240.

(Continued)

*Primary Examiner* — Valarie E Bertoglio
(74) *Attorney, Agent, or Firm* — Rimon, P.C.

(57) ABSTRACT

Provided in the present invention is a method for inducing pluripotent stem cells to differentiate into ventricular myocytes in vitro, which is achieved by maintaining, amplifying and culturing pluripotent stem cells in vitro, adding a substance capable of activating the Smad1/5/8 signaling pathway directly or indirectly into the culture medium when pluripotent stem cells are in the middle stage of myocardial differentiation, i.e. the period of differentiating into cardiac muscle cells from mesoderm cells or myocardial precursor cells, which enables stem cells to differentiate into ventricular myocytes directionally. Ventricular myocytes with biological activity and function are obtained successfully by means of the method of the present invention, which reveals the regulatory mechanism during differentiation of myocardial precursor cells into ventricular myocytes; moreover, the human ventricular myocytes obtained via differentiation can be widely used in treating myocardial infarction by cell transplantation, in toxicological analysis of the heart and in the development of heart-related drugs.

23 Claims, 10 Drawing Sheets

(56) References Cited

U.S. PATENT DOCUMENTS

| | | | | |
|---|---|---|---|---|
| 2009/0269314 A1* | 10/2009 | Keller | ............... | C12N 5/0657 |
| | | | | 424/93.7 |
| 2010/0166713 A1 | 7/2010 | Dalton et al. | | |
| 2013/0189785 A1* | 7/2013 | Palecek | ............... | C12N 5/0657 |
| | | | | 435/377 |
| 2015/0299658 A1 | 10/2015 | Ma | | |
| 2016/0122719 A1 | 5/2016 | Ma | | |
| 2021/0002614 A1 | 1/2021 | Ma | | |

FOREIGN PATENT DOCUMENTS

| | | | |
|---|---|---|---|
| CA | 2395950 | A1 | 7/2011 |
| CA | 2802526 | A1 | 12/2011 |
| CA | 2802526 | C | 11/2021 |
| CN | 1863904 | | 11/2006 |
| CN | 1969040 | | 5/2007 |
| CN | 101074428 | | 11/2007 |
| CN | 101641436 | | 2/2010 |
| CN | 101720355 | | 6/2010 |
| EP | 1 674 562 | | 6/2006 |
| EP | 1674562 | A1 | 6/2006 |
| EP | 2580317 | A1 | 4/2013 |
| EP | 2891712 | A1 | 7/2015 |
| EP | 2580317 | B1 | 12/2020 |
| JP | 2003526677 | A1 | 9/2003 |
| JP | 2006-517092 | | 7/2006 |
| JP | 2006-523091 | | 10/2006 |
| JP | 2007-532103 | | 11/2007 |
| JP | 2009-524484 | | 7/2009 |
| JP | 2009-171981 | | 8/2009 |
| JP | 2009531054 | A | 9/2009 |
| JP | 2009-535058 | | 10/2009 |
| JP | 2010508846 | A | 3/2010 |
| JP | 2011-517563 | | 6/2011 |
| JP | 6412868 | B2 | 10/2018 |
| JP | 6427126 | B2 | 11/2018 |
| WO | 2002081729 | A2 | 10/2002 |
| WO | WO-2004/050894 | | 6/2004 |
| WO | WO-2004/081205 | | 9/2004 |
| WO | WO-2004/098490 | | 11/2004 |
| WO | WO-2005/033298 | | 4/2005 |
| WO | WO-2005/098425 | | 10/2005 |
| WO | WO-2007/087355 | | 8/2007 |
| WO | WO-2007/130474 | | 11/2007 |
| WO | WO-2008/054819 | | 5/2008 |
| WO | WO-2008/112323 | | 9/2008 |
| WO | WO 2009/036982 | | 3/2009 |
| WO | WO-2009/075954 | | 6/2009 |
| WO | WO-2010/007031 | | 1/2010 |
| WO | 2011056416 | A2 | 5/2011 |
| WO | 2011157029 | A1 | 12/2011 |
| WO | WO-2011/157029 | | 12/2011 |
| WO | WO 2011157029 | * | 12/2011 |
| WO | 2013056072 | A1 | 4/2013 |
| WO | WO-2013/056072 | | 4/2013 |
| WO | WO 2013159349 | * | 10/2013 |
| WO | WO-2014/015777 | | 1/2014 |
| WO | WO-2015058117 | A1 * | 4/2015 ......... G01N 33/5061 |

OTHER PUBLICATIONS

Laflamme et al., "Cardiomyocytes derived from human embryonic stem cells in pro-survival factors enhance function of infarcted rat hearts," Nat Biotechnol (2007) 25(9):1015-1024.
Takahashi et al., "Induction of pluripotent stem cells from adult human fibroblasts by defined factors," Cell (2007) 131(5):861-872.
Thomson et al., "Embryonic stem cell lines derived from human blastocysts," Science (1998) 282:1145-1147.
Yang et al., "Human cardiovascular progenitor cells develop from a KDR+ embryonic-stem-cell-derived population," Nature (2008) 453(7194):524-528.
Yu et al., "Induced pluripotent stem cell lines derived from human somatic cells," Science (2007) 218(5858):1917-1920.
Zhang et al., "Direct differentiation of atrial and ventricular myocytes from human embryonic stem cells by alternating retinoid signals," Cell Res (2011) 21(4):579-587.
Communication pursuant to Article 94(3) EPC for EP 10 853 137.7, dated Oct. 13, 2016, 7 pages.
Müller et al., "Selection of ventricular-like cardiomyocytes from ES cells in vitro," The FASEB Journal (2000) 14:2540-2548.
International Preliminary Report on Patentability for PCT/CN2013/079811, dated Jan. 27, 2015, 27 pages.
Office Action for CA 2,802,526, dated Aug. 31, 2016, 4 pages.
BIO, WNT pathway activator; Inhibits GSK3, available from https://www.stemcell.com/bio.html, accessed Oct. 19, 2016, 9 pages.
Fukuda et al., "Stem Cells as a Source of Regenerative Cardiomyocytes," Circ Res (2006) 98:1002-1013.
Communication pursuant to Article 94(3) EPC for EP 13 823 221.0, dated Mar. 29, 2017, 5 pages.
Office Action for JP 2015-523397, dated Jun. 1, 2017, 6 pages (Including English translation).
Restriction Requirement for U.S. Appl. No. 14/925,829, dated Apr. 4, 2017, 9 pages.
Response to Examination Report for CA 2 802 526, dated Feb. 28, 2017, 3 pages.
Examination Report for CA 2 802 526, dated Jul. 6, 2017, 4 pages.
Response to Communication pursuant to Article 94(3) EPC for EP 10 853 137.7, dated Apr. 24, 2017, 13 pages.
First Examination Report for AU 2015230768, dated Jan. 20, 2017, 6 pages.
Response to Office Action for JP 2016-016994, dated Jun. 20, 2017, 7 pages.
Bao et al., "Regulation of chamber-specific gene expression in the developing heart by Irx4," Science (1999) 283:1161-1164.
Boheler et al., "Differentiation of pluripotent embryonic stem cells into cardiomyocytes," Circulation Research (2002) 91:189-201.
Broach, et al., "High throughput screening for drug discovery," Nature (1996) 384:14-16.
Burbaum, et al., "New technologies for high-throughput screening," Curr. Opin. Chem. Biol. (1997) I:72-78.
Cao et al., "Highly efficient induction and long-term maintenance of multipotent cardiovascular progenitors from human pluripotent stem cells under defined conditions," Cell Research (2013) 23:1119-1132.
Chambers, et al., "Functional expression cloning of Nanog, a pluripotency sustaining factor in embryonic stem cells," Cell (2003) 13(5): 643-55.
Chen et al., "Electrophysiological challenges of cell-based myocardial repair," Circulation (2009) 120:2496-2508.
Cheng et al., "Calcium sparks," Physiol Rev (2008) 88:1491-1545.
Chong et al., "Human embryonic-stem-cell-derived cardiomyocytes regenerate non-human primate hearts," Nature (2014) 510:273-277.
Cleemann et al., "Two-dimensional confocal images of organization, density, and gating of focal Ca2+ release sites in rat cardiac myocytes," Proc Natl Acad Sci USA (1998) 95:10984-10989.
Communication pursuant to Article 94(3) EPC for EP 10 853 137.7, dated May 6, 2015, 4 pages.
Cornell et al., "Activin-mediated mesoderm induction requires FGF," Development (1994) 120:453-462.
Domian et al., "Generation of functional ventricular heart muscle from mouse ventricular progenitor cells," Science (2009) 326:426-429.
Examination Report (Australia) for AU 2010355614, dated Sep. 13, 2013.
Fernandes, "Letter from the society president," J Biomol. Screening (1997) 2:1.
First Office Action for CN 201080067389.1, dated Jan. 26, 2014, 5 pages.
Fourth Amendment in Response to Examination Report for AU 2010355614, filed Jun. 5, 2015, 8 pages.
Fu et al., "Na+/Ca2+ exchanger is a determinant of excitation-contraction coupling in human embryonic stem cell-derived ventricular cardiomyocytes," Stem Cells Dev (2010) 19(6):773-782.
Gassanov et al., "Endothelin induces differentiation of ANP-EGFP expressing embryonic stem cells towards a pacemaker phenotype," FASEB Journal (2004) 18:1710-1712 (online version).

(56) References Cited

OTHER PUBLICATIONS

Gassanov et al., "Retinoid acid-induced effects on atrial and pacemaker cell differentiation and expression of cardiac ion channels," Differentiation (2008) 76:971-980.
Hao et al., "Dorsormorphin, a selective small molecule inhibitor of BMP signaling, promotes cardiornyogenesis in embryonic stern cells," PLoS One (2008) 3:e2904.
Hochgreb et al., "A caudorostral wave of RALDH2 conveys anteroposterior information to the cardiac field," Development (2003) 130:5363-5374.
Honda et al., "RXR agonist enhances the differentiation of cardiomyocytes derived from embryonic stem cells in serum-free conditions," Biochemical and Biophysical Research Communications (2005) 333:1334-1340.
Hong et al., "Development of efficient cardiac differentiation method of mouse embryonic stem cells," Key Engineering Materials (2007) 342-343:25-28.
International Preliminary Report on Patentability for PCT/CN2010/078645, dated Dec. 14, 2012, 7 pages.
International Search Report for PCT/CN2010/078645, dated Mar. 24, 2011, 4 pages.
Itsykson et al., "Derivation of neural precursors from human embryonic stem cells in the presence of noggin," Mol Cell Neurosci (2005) 30:24-36.
Janzen et al., "High throughput screening as a discovery tool in the pharmaceutical industry," Lab Robotics Automation (1996) pp. 8261-8265.
Keegan, "Retinoic acid signaling restricts the cardiac progenitor pool," Science (2005) 307:247-249.
Kehat et al., "Electromechanical integration of cardiomyocytes derived from human embryonic stem cells," Nat Biotechnol (2004) 22:1282-1289.
Kehat et al., "Human embryonic stem cells can differentiate into myocytes with structural and functional properties of cardiomyocytes," J Clin Invest (2001) 108(3):407-414.
Kennedy et al., "Retinoic acid enhances skeletal muscle progenitor formation and bypasses inhibition by bone morphogentic protein 4 but not dominant negative β-catenin," BMC Biology (2009) 7:67, 21 pages.
Korol et al., "A novel activity of the Dickkopf-1 amino terminal domain promotes axial and heart development independently of canonical Wnt inhibition," Dev Biol (2008) 324:131-138.
Lu et al., "Avian-induced pluripotent stem cells derived using human reprogramming factors," Stem Cells Dev. (2012) 21 (3): 394-403.
Maltsev et al., "Embryonic stern cells differentiate in vitro into cardiomyocytes representing sinusnodal, atrial and ventricular cell types," Mech Dev (1993) 44:41-50.
Mandenius et al., "Cardiotoxicity testing using pluripotent stem cell-derived human cardiomyocytes and state-of-the-art bioanalytics: a review," J. Appl. Toxicol. (2011) 31:191-205.
Marvin et al., "Inhibition of Wnt activity induces heart formation from posterior mesoderm," Genes Dev (2001) 15:316-327.
Mummery et al. "Differentiation of human embryonic stem cells to cardiomyocytes: role of coculture with visceral endoderm-like cells." Circulation (2003) 107:2733-2740.
Niederreither et al., "Embryonic retinoic acid synthesis is essential for heart morphogenesis in the mouse," Development (2001) 128:1019-1031.
Nogrady, Medicinal Chemistry A Biochemical Approach, Oxford University Press, New York (1985) pp. 388-392.
Notice of Acceptance for AU 2010355614, dated Jun. 22, 2015, 2 pages.
Notification of Reasons for Rejection (translation) for JP 2013-514527, dated Jan. 27, 2015, 7 pages.
Notification of Decision of Rejection (with translation) for JP 2013-514527, dated Sep. 25, 2015, 15 pages.
Orts-Llorca et al., "Determination of heart polarity (atierio venous axis) in the chicken embryo," Raux Arch Entwick-Iungsmechanik (1967) 113:17.
Pain et al., "Long-term in vitro culture and characterisation of avian embryonic stem cells with multiple morphogenetic potentialities," Development (1996) 122:2339-2348.
Patent Examination Report No. 2 for AU 2010355614, dated Sep. 16, 2014, 5 pages.
Patent Examination Report No. 3 for AU 2010355614, dated Feb. 17, 2015, 4 pages.
Patwardhan et al., "The rostro-caudal position of cardiac myocytes affect their fate," Dev Dyn (2000) 218:123-135.
Picht et al., "SparkMaster: automated calcium spark analysis with Image," Am J Physiol Cell Physiol (2007) 293:C1073-C1081.
Reppel et al., "Effect of cardioactive drugs on action potential generation and propagation in embryonic stem cell-derived cardiomyocytes," Cell Physiol Biochem (2007) 19:213-224.
Response to Communication pursuant to Rules 70(2) and 70a(2) EPC for EP 10 853 137.7, filed Aug. 5, 2014, 13 pages.
Response to First Office for CN 2010800673891, 14 pages.
Response to Second Office Action for CN 2010800673891, 76 pages.
Schneider et al., "Wnt antagonism initiates cardiogenesis in Xenopus laevis," Genes Dev (2001) 15:304-315.
Schulze et al., "BMS-189453, a novel retinoid receptor antagonist, is a potent testicular toxin," Toxicol Sci (2001) 59:297-308.
Second Amendment in Response to Examination Report for AU 2010355614, filed Aug. 26, 2014, 18 pages.
Second Office Action for CN 201080067389.1, dated Oct. 11, 2014, 10 pages.
Shimoji et al., "G-CSF promotes the proliferation of developing cardiornyocytes in vivo and in derivation from ESCs and iPSCs," Cell Stem Cell (2010) 6:227-237.
Shinzo (Heart's Selection 1) (2005) 37(12):990-993 (English translation of introduction).
Shiraki et al., "Differentiation and characterization of embryonic stem cells into three germ layers," Biochemical and Biophysical Research Communications (2009) 381(4):694-699.
Supplementary European Search Report for EP 10853137.7, dated Jan. 14, 2014, 9 pages.
Supplementary European Search Report for EP 13823221.0, dated Mar. 4, 2016, 10 pages.
Tesar et al., "New cell lines from mouse epiblast share defining features with human embryonic stem cells," Nature (2007) 448:196-199.
Third Amendment in Response to Examination Report No. 2 for AU 2010355614, filed Jan. 30, 2015, 12 pages.
Third Office Action for CN 201080067389.1, dated May 26, 2015, 10 pages.
Tran et al., "Wnt3a-induced mesoderm formation and cardiomyogenesis in human embryonic stem cells," Stem Cells (2009) 27:1869-1878.
Ueno et al., "Biphasic role for Wnt/β-catenin signaling in cardiac specification in zebrafish and embryonic stem cells," PNAS (2007) 104(23):9685-9690.
Van Wijk et al., "Role of bone morphogentic proteins in cardiac differentiation", Cardiovascular Research (2007) 74:244-255.
Wobus et al., "Retinoic acid accelerates embryonic stem cell-derived cardiac differentiation and enhances development of ventricular cardiomyocytes," J Mol Cell Cardiol (1997) 29:1525-1539.
Woo et al., "Spatiotemporal characteristics of junctional and nonjunctional focal Ca2+ release in rat atrial myocytes," Circ Res (2003) 92:e1-11.
Written Opinion for PCT/CN2010/078645, dated Mar. 24, 2011, 18 pages.
Xavier-Neto et al., "A retinoic acid-inducible transgenic marker of sino-atrial development in the mouse heart," Development (1999) 126:2677-2687.
Xavier-Neto et al., "Retinoid signaling and cardiac anteroposterior segmentation," Genesis (2001) 31:97-104.
Xu et al., "Basic FGF and suppression of BMP signaling sustain undifferentiated proliferation of human ES cells," Nat Methods (2005) 2:185-190.
Xu et al., "BMP4 initiates human embryonic stem cell differentiation to trophoblast," Nat Biotechnol (2002) 20:1261-1264.

(56) References Cited

OTHER PUBLICATIONS

Xu, "Differentiation and enrichment of cardiomyocytes from human pluripotent stem cells," Journal of Molecular and Cellular Cardiology (2012) 52:1203-1212.
Xu et al., "Feeder-free growth of undifferentiated human embryonic stem cells," Nat Biotech (2001) 19:971-974.
Yanagita, "BMP antagonists: their roles in development and involvement in pathophysiology," Cytokine Growth Factor Rev (2005) 16:309-317.
Ying et al., "BMP induction of Id proteins suppresses differentiation and sustains embryonic stem cell self-renewal in collaboration with STAT3," Cell (2003) 115:281-292.
Yuasa and Fukuda, "Cardiomyocyte Differentiation from Embryonic Stem Cells," Experimental Medicine (2008) 26(5)(extra edition):787-792 (with partial translation).
Yuasa et al., "Transient inhibition of BMP signaling by Noggin induces cardiomyocyte differentiation of mouse embryonic stem cells," Nat Biotechnol (2005) 23:607-611.
Yutzey et al., "Diversification of cardiornyogenic cell lineages in vitro," Dev Biol (1995) 170:531-541.
Zhang et al. "Short-term BMP-4 treatment initiates mesoderm induction in human embryonic stem cells." Blood (2008) 111(4):1933-1941.
Zhu et al., "Neuregulin/ErbB Signaling Regulates Cardiac Subtype Specification in Differentiating Human Embryonic Stem Cells," Circ Res (2010) 107(6):776-786.
Restriction Requirement for U.S. Appl. No. 13/703,608, dated Jun. 27, 2013, 10 pages.
Response to Restriction Requirement for U.S. Appl. No. 13/703,608, filed Jul. 26, 2013, 11 pages.
Office Action for U.S. Appl. No. 13/703,608, dated Sep. 13, 2013, 32 pages.
Response to Office Action for U.S. Appl. No. 13/703,608, filed Mar. 13, 2014, 20 pages.
Final Rejection for U.S. Appl. No. 13/703,608, dated Jul. 10, 2014, 19 pages.
Response to Final Rejection for U.S. Appl. No. 13/703,608, filed Sep. 9, 2014, 15 pages.
Advisory Action for U.S. Appl. No. 13/703,608, dated Oct. 1, 2014, 3 pages.
Request for Continued Examination for U.S. Appl. No. 13/703,608, filed Nov. 7, 2014, 3 pages.
Notice of Allowance for U.S. Appl. No. 13/703,608, dated Jun. 23, 2015, 11 pages.
Notice of Allowance for U.S. Appl. No. 13/703,608, dated Jul. 30, 2015, 4 pages.
Response to Notice of Allowance for U.S. Appl. No. 13/703,608, filed Sep. 23, 2015, 10 pages.
Response to Notice of Allowance for U.S. Appl. No. 13/703,608, filed Oct. 8, 2015, 4 pages.
Notice of Allowance for U.S. Appl. No. 13/703,608, dated Nov. 4, 2015, 4 pages.
Notice of Allowance for U.S. Appl. No. 13/703,608, dated Feb. 3, 2016, 2 pages.
Braam et al. "Prediction of drug-induced cardiotoxicity using human embryonic stem cell-derived cardiomyocytes," Stem Cell Research (2010) 4, 107-116.
Cao et al. "Transcriptional and functional profiling of human embryonic stem cell-derived cardiomyocytes", PloS One, 2008, 3(10), e3474.
Hen et al. "Pretreatment of Measenchymal Stem Cells With a Combination of Growth Factors Enhances Gap Junction Formation, Cytoprotective Effect On Cardiomyocytes, and Therapeutic Efficacy for Myocardial Infarction", Journal of the American College of Cardiology, 2008, vol. 51, No. 9, pp. 933-943 doi:10.1016/j.jacc.2007.11.040.
Kastner et al. "Vitamin A deficiency and mutations of RXRα, RXRβ and RARα lead to early differentiation of embryonic ventricular cardiomyocytes," Development 124, 4749-4758 (1997) https://dev.biologists.org/content/124/23/4749.article-info.

Lee et al. "Human Pluripotent Stem Cell-Derived Atrial and Ventricular Cardiomyocytes Develop from Distinct Mesoderm Populations", Cell Stem Cell 21, Aug. 3, 2017, pp. 179-194 http://dx.doi.org/10.1016/j.stem.2017.07.003.
Nalto et al. "Developmental stage-specific biphasic roles of Wnt/B-catennin signaling in cardiomyogenesis and hematopoiesis," PNAS, Dec. 26, 2006, vol. 103, No. 52, pp. 19812-19817 doi/10.1073/pnas.0605768103.
Pei et al. "Chemical-defined and albumin-free generation of human atrial and ventricular myocytes from human pluripotent stem cells," Stem Gell Research, 19 (2017) 94-103 http://dx.doi.org/10.1016/j.scr.2017.01.006.
Rosenthal et al. "From the bottom of the heart: anteroposterior decisions in cardiac muscle differentiation," Cell Biology 2000, 12:742-746.
Wobus et al. "In vitro cellular models for cardiac development and pharmacotoxicology," Toxicology in Vitro, vol. 9, Issue 4, Aug. 1995, pp. 477-483, 485-488 (abstract) https://doi.org/10.1016/0887-2333(95)00023-2.
Gassanov et al., "Retinoid acid-induced effects on atrial and pacemaker cell differentiation and expression of cardiac ion channels," Differentiation (2008) 76:971-980 doi:10.1111/j.1432-0436.2008.00283.X.
He et al., "Human Embryonic Stem Cells Develop Into Multiple Types of Cardiac Myocytes—Action Potential Characterization," Circ Res. 2003;93:32-39 doi:10.1161/01.RES.0000080317.92718.99.
Lewis et al., "Dkk1 and Wnt3 interact to control head morphogenesis in the mouse," Development 135, 1791-1801 (2008) doi:10.1242/dev.018853.
Mo et al., "Inhibition of the Wnt palmitoyltransferase porcupine suppresses cell growth and downregulates the Wnt/B-catenin pathway in gastric cancer," Oncology Letters 5: 1719-1723, 2013 doi:10.3892/ol.2013.1256.
Nansi et al., "Isolation of Human Ventricular and Atrial Cardiomyocytes:Technical Note," Cardioscience vol. 4 No.2, Jun. 1993, p. 111-116.
Narayanan et al., "Antagonistic Effect of Small-molecule Inhibitors of Wnt/B-catenin in Multiple Myeloma," Anticancer Research 32:4697-4708 (2012).
Steimle et al., "TBX5: A Key Regulator of Heart Development," Curr Top Dev Biol. 2017; 122: 195-221 doi:10.1016/bs.ctdb.2016.08.008.
Wobus et al., "Retinoic Acid Accelerates Embryonic Stem Cell-Derived Cardiac Differentiation and Enhances Development of Ventricular Cardiomyocytes," J Mol Cell Cardiol 29, 1525-1539 (1997).
Xavier-Neto et al., "A retinoic acid-inducible transgenic marker of sino-atrial development in the mouse heart," Development 126, 2677-2687 (1999).
Yuasa et al., "Transient inhibition of BMP signaling by Noggin induces cardiomyocyte differentiation of mouse embryonic stem cells," nature biotechnology vol. 23, No. 5, May 2005, p. 607-611 doi:10.1038/nbt1093.
Zhang et al., "Direct differentiation of atrial and ventricular myocytes from human embryonic stem cells by alternating retinoid signals," Cell Research (2011) 21:579-587 doi:10.1038/cr.2010.163.
Zhang et al., "Short-term BMP-4 treatment initiates mesoderm induction in human embryonic stem cells," Blood, Feb. 15, 2008, vol. 111, No. 4, p. 1933-1941 doi:10.1182/blood.2007-02-074120.
Communication pursuant to Article 94(3) EPC for European patent application EP13 823 221.0, dated Mar. 29, 2017, 5 pages.
Responsive to the communication pursuant to Article 94(3) EPC for European patent application EP13 823 221.0, dated Oct. 4, 2017, 12 pages.
Communication pursuant to Article 94(3) EPC for European patent application EP13 823 221.0, dated Mar. 16, 2018, 4 pages.
Communication pursuant to Article 94(3) EPC for European patent application EP13 823 221.0, dated Dec. 18, 2018, 3 pages.
Responsive to the communication pursuant to Article 94(3) EPC for European patent application EP13 823 221.0, dated Mar. 6, 2019, 8 pages.

(56) References Cited

OTHER PUBLICATIONS

Communication pursuant to Article 94(3) EPC for European patent application EP13 823 221.0, dated Sep. 27, 2019, 4 pages.
Amended claims (clear version) for European patent application EP13 823 221.0, dated Jul. 25, 2018, 3 pages.
Office action for Japanese patent application JP2015-523397, dated Feb. 27, 2018, 4 pages.
Notice of reasons for rejection for Japanese patent application JP2015-523397, dated Feb. 27, 2018, 6 pages.
Amended claims (marked-up version) for Japanese patent application JP2015-523397, dated Aug. 24, 2018, 6 pages.
Amendment as filed for Japanese patent application JP2015-523397, dated Aug. 24, 2018, 4 pages.
Argument as filed for Japanese patent application JP2015-523397, dated Aug. 24, 2018, 6 pages.
Notice of allowance for Japanese patent application JP2015-523397, dated Sept. 4, 2018, 3 pages.
Claims for European patent application EP10 853 137.7, dated Jan. 31, 2020, 4 pages.
Claims (clean version) for European patent application EP10 853 137.7, dated Jan. 31, 2020, 3 pages.
Description for European patent application EP10 853137.7, dated Jan. 31, 2020, 1 page.
Responsive to the communication pursuant to Article 94(3) EPC for European patent application EP10 853137.7, dated Jan. 31, 2020, 3 pages.
Patented claims for Japanese patent application JP2016-016994, dated Nov. 21, 2018, 3 pages.
Response to Examination Report for Australian patent application AU2013295940, dated Dec. 13, 2018, 40 pages.
Notice of grant for patent for Australian patent application AU2013295940, dated May 16, 2019, 2 pages.
Responsive to the communication pursuant to Article 94(3) EPC for EP13 823 221.0, dated Jul. 26, 2018, 10 pages.
Amended claims (marked-up version) for Japanese patent application JP2015-523397, dated Dec. 1, 2017, 9 pages.
Response to 2nd Office Action for Japanese patent application JP2015-523397, dated Aug. 24, 2018, 10 pages in English.
Response to Office Action for Japanese patent application JP2016-016994, dated Jun. 20, 2017, 7 pages.
Office Action for Japanese patent application JP2015-523397, dated Jun. 1, 2017, 6 pages with extra 3 pages of English language equivalent or summary.
Notice of Allowance and Fee(s) Due for U.S. Appl. No. 14/925,829, dated Oct. 29, 2019, 16 pages.
Response to Office Communication Concerning the Application for U.S. Appl. No. 14/925,829, dated Jan. 27, 2020, 13 pages.
Office Action for Canadian patent application CA 2,802,526, dated May 1, 2020, 5 pages.
Response and Amendment for Canadian patent application CA 2,802,526, dated Oct. 30, 2020, 6 pages.
Claims (clear version) for Canadian patent application CA 2,802,526, dated Oct. 30, 2020, 5 pages.
Claims (marked up version—not for replacement) for Canadian patent application CA 2,802,526, dated Oct. 30, 2020, 7 pages.
Appendix A: Confirmatory Supporting Data for Canadian patent application CA 2,802,526, dated Oct. 30, 2020, 2 pages.
Notice of Allowance for Application for Canadian patent application CA 2,802,526, dated May 31, 2021, 1 pages.
Response to the communication pursuant to Article 94(3) EPC for European patent application EP10 853 137.7, dated Jan. 31, 2020, 3 pages.
Claims (clear version) for European patent application EP10 853 137.7, dated Jan. 31, 2020, 3 pages.
Claims (marked-up version) for European patent application EP10 853137.7, dated Jan. 31, 2020, 4 pages.
Description (clean version) for European patent application EP10 853 137.7, dated Jan. 31, 2020, 1 pages.
Description (marked-up version) for European patent application EP10 853 137.7, dated Jan. 31, 2020, 1 pages.
Communication under Rule 71(3) EPC for European patent application EP10 853 137.7, dated Jun. 9, 2020, 53 pages.
Responsive to the communication pursuant to Article 94(3) EPC for European patent application EP13 823 221.0, dated Apr. 7, 2020, 7 pages.
Claims (clean version) for European patent application EP13 823 221.0, dated Apr. 7, 2020, 3 pages.
Claims (marked-up) for European patent application EP13 823 221.0, dated Apr. 7, 2020, 3 pages.
Communication pursuant to Article 94(3) EPC for European patent application EP13 823 221.0, dated Oct. 15, 2020, 4 pages.
Responsive to the Communication pursuant to Article 94(3) EPC for European patent application EP13 823 221.0, dated Apr. 21, 2021, 8 pages.
Claims (clean version) for European patent application EP13 823 221.0, dated Apr. 21, 2021, 3 pages.
Claims (marked-up version) for European patent application EP13 823 221.0, dated Apr. 21, 2021, 3 pages.
Exhibit 4 in response (Figure-A) for European patent application EP13 823 221.0, dated Apr. 21, 2021, 1 page.
Communication including the Extended European Search Report for European patent application EP20213862.4, dated Jun. 22, 2021, 11 pages.
Office Action for Canadian patent application CA2,886,396, dated Feb. 6, 2020, 5 pages.
Response to Office Action for Canadian patent application CA 2,886,396, dated Aug. 6, 2020, 45 pages.
Claims (clean version) for response to Office Action for Canadian patent application CA 2,886,396, dated Aug. 6, 2020, 7 pages.
Office Action for Canadian patent application CA 2,886,396, dated Mar. 12, 2021, 5 pages.
Response to Office Action for Canadian patent application CA 2,886,396, dated Jul. 8, 2021, 17 pages.
Claims (clean version) for response to Office Action for Canadian patent application CA 2,886,396, dated Jul. 8, 2021, 6 pages.
Final rejection for U.S. Appl. No. 14/925,829, dated Jun. 22, 2018, 18 pages.
Amendment in response to final office action for U.S. Appl. No. 14/925,829, dated Dec. 20, 2018, 12 pages.
Amendment in response to final office action for U.S. Appl. No. 14/925,829, dated Jul. 24, 2019, 17 pages.
Examiner interview summary record for U.S. Appl. No. 14/925,829, dated Oct. 29, 2019, 1 page.
Notice of Allowance for U.S. Appl. No. 14/925,829, dated Oct. 29, 2019, 16 pages.
Response to office communication concerning the application for U.S. Appl. No. 14/925,829, dated Dec. 27, 2020, 13 pages.
Response to Rule 312 Communication for U.S. Appl. No. 14/925,829, dated Dec. 24, 2020, 2 pages.
Issue notification for U.S. Appl. No. 14/925,829, dated Feb. 27, 2020, 1 page.
Non-final office action for U.S. Appl. No. 14/925,829, dated Jan. 25, 2019, 20 pages.
Description (clean version) for U.S. Appl. No. 14/925,829, dated Jan. 3, 2020, 1 page.
Office action for European patent application EP10 853 137.7, dated Jul. 25, 2018, 3 pages.
Response to office action for European patent application EP10 853 137.7, dated Jan. 29, 2019, 50 pages.
Communication pursuant to Article 94(3) EPC for European patent application EP10 853 137.7, dated Jul. 29, 2019, 3 pages.
Description (marked-up version) for European patent application EP10 853 137.7, dated Jan. 31, 2020, 1 page.
Amended claims for Japanese patent application JP2016-016994, dated Mar. 26, 2018, 3 pages.
Response for Japanese patent application JP2016-016994, dated Mar. 26, 2018, 7 pages.
Office action for Japanese patent application JP2016-016994, dated Aug. 8, 2018, 4 pages.
Amended claims for Japanese patent application JP2016-016994, dated Aug. 14, 2018, 3 pages.
Patented claims for Japanese patent application JP2016-016994, dated Aug. 14, 2018, 3 pages.

(56) References Cited

OTHER PUBLICATIONS

Response for Japanese patent application JP2016-016994, dated Aug. 14, 2018, 5 pages.
Notice of allowance for Japanese patent application JP2016-016994, dated Sep. 27, 2018, 3 pages.
1st examination report for Australian patent application AU2013295940, dated Jan. 22, 2018, 5 pages.
Response to 1st examintion report for Australian patent application AU2013295940, dated Dec. 13, 2018, 40 pages.
2nd examination report for Australian patent application AU2013295940, dated Jan. 9, 2019, 3 pages.
Amendment claims (clean version) for Australian patent application AU2013295940, dated Jan. 15, 2019, 5 pages.
Response to 2nd examination report for Australian patent application AU2013295940, dated Jan. 15, 2019, 34 pages.
Notice of acceptance for Australian patent application AU2013295940, dated Jan. 21, 2019, 3 pages.
Claims as accepted for Australian patent application AU2013295940, dated Jan. 22, 2019, 5 pages.
Published specifications for Australian patent application AU2013295940, dated May 17, 2019, 49 pages.
Response and amendment for Canadian patent application CA2,802,526, dated Jan. 5, 2018, 5 pages.
Office action for Canadian patent application CA2,802,526, dated May 8, 2018, 4 pages.
Notice of abandonment for Canadian patent application CA2,802,526, dated Dec. 20, 2018, 1 page.
Claims for Canadian patent application CA2,802,526, dated Nov. 7, 2019, 6 pages.
Request to reinstate for Canadian patent application CA2,802,526, dated Nov. 7, 2019, 6 page.
Notice of reinstatement for Canadian patent application CA2,802,526, dated Nov. 27, 2019, 1 page.
Office action for Canadian patent application CA2,802,526, dated Mar. 22, 2019, 4 pages.
Amended claims (clean version) for Canadian patent application CA2,802,526, dated Sep. 19, 2019, 8 pages.
Response as filed for Canadian patent application CA2,802,526, dated Sep. 19, 2019, 33 pages.
Office action for Canadian patent application CA2,802,526, dated Feb. 6, 2020, 5 pages.

* cited by examiner

METHOD FOR INDUCING PLURIPOTENT STEM CELLS TO DIFFERENTIATE INTO VENTRICULAR MYOCYTES IN VITRO

This application is the national phase of PCT application PCT/CN2013/079811 having an international filing date of Jul. 22, 2013, entitled "METHOD FOR INDUCING PLURIPOTENT STEM CELLS TO DIFFERENTIATE INTO VENTRICULAR MYOCYTES IN VITRO," which claims priority to Chinese Application No. 20120257088.6, filed Jul. 23, 2012. The contents of the above applications are incorporated herein by this reference in their entireties.

TECHNICAL FIELD

In certain aspects, the present invention relates to the fields of pluripotent stem cell (PSC) differentiation and signal transduction. In specific embodiments, the present invention involves methods to induce differentiation of PSCs into ventricular myocytes (VMs) in vitro.

BACKGROUND

In mammals, cardiomyocytes (CMs) are capable of cell division and proliferation before birth. However, their ability to proliferate rapidly declines after birth. Adult CMs typically have a very poor ability to proliferate. In heart diseases associated with cardiac tissue necrosis such as myocardial infarction, the consequent decline in cardiac function is typically irreversible because adult CMs have lost their ability to proliferate and are unable to repair necrotic tissue. Although medications can be used to increase cardiac contractility and improve the ability of the heart to pump blood, the heavier burden on the heart may in turn worsen the condition. Replacement of necrotic cells by transplantation of normal CMs is one of the methods for treatment of heart infarction and similar diseases or conditions. Because adult CMs have almost no ability to proliferate, a source of human CMs is apparently needed for regenerative medicine, for example, for treating myocardial infarction.

Pluripotent stem cells (PSCs) include embryonic stem cells (ESCs) and induced pluripotent stem cells (iPSCs). See, Thomson J A et al., Embryonic stem cell lines derived from human blastocysts, *Science*, 1998, 282:1145-1147; Yu J et al., Induced pluripotent stem cell lines derived from human somatic cells, *Science*, 2007, 318:1917-1920; and Takahashi K et al., Induction of pluripotent stem cells from adult human fibroblasts by defined factors, *Cell*, 2007, 131:861-872, the contents of which are incorporated herein by reference in their entireties. These pluripotent stem cells not only possess a strong ability to self-renew but also have the potentials for differentiation into CMs. Thus, PSC is one of the most promising cell sources of CMs if an efficient cardiac differentiation method is established.

In general, there are two methods to induce differentiation of CMs from PSCs. In one method, PSCs are cultured in suspension to form embryoid bodies that differentiate into numerous cell types including CMs. In the other method, monolayer PSCs under ordinary culture conditions are directly differentiated into CMs. A variety of cytokines have been reported to improve the efficiency of cardiac differentiation, and their dosages and duration of action vary based on the different differentiation systems.

Human PSC-derived CMs typically include three main types: nodal cells, VMs, and atrial myocytes (AMs). See, He J Q et al., Human embryonic stem cells develop into multiple types of cardiac myocytes: Action potential characterization, *Circ Res*. 2003, 93:32-39, the content of which is incorporated herein by reference in its entirety. According to their functional properties, fully mature CMs can be subdivided into working CMs and spontaneous beating nodal cells. Working CMs, including AMs and VMs that constitute the majority of the atrial and ventricular muscle walls, contain abundant myofibrils and possess the properties of conductivity and excitability, and perform systolic functions of the heart. Nodal cells spontaneously generate excitability, which controls the beating activity of heart. Similar to working CMs, the nodal cells possess the properties of conductivity and excitability, but typically have lost contractility. AMs, VMs, and nodal cells exhibit significant differences in the composition of intracellular myofibrils and cell membrane expression of ion channel proteins, resulting in substantial differences in their action potentials (APs) and their rhythmic contraction. For cell transplantation therapies for heart disease, it is essential to transplant cardiomyocytes with an appropriate subtype of high purity. For example, repairing ventricular tissue requires transplantation of VMs of high purity, which determines whether the cells can successfully integrate into the recipient heart tissue, improve heart functions, and reduce side effects such as arrhythmia caused by the transplanted cells. If the subtype of transplanted cardiomyocytes does not match the type of the tissue they are transplanted into, or the purity of transplanted CMs is not sufficient, arrhythmia may occur, impairing the function of the recipient heart. The left ventricle, which mainly carries the body blood supply, has the largest volume, thickest muscle walls, and strongest pumping capacity. Additionally, myocardial infarction occurs primarily in the left ventricle. Thus, among the three types of CMs, VMs are of the most significance for cell transplantation therapy of myocardial infarction. See, Chen H S et al., Electrophysiological challenges of cell-based myocardial repair, *Circulation*, 2009, 120:2496-250, the content of which is incorporated herein by reference in its entirety.

Obtaining large numbers of human CMs is important for the development of drugs for heart diseases, and the assessment of cardiac-toxicity of drugs. Adult human CMs cannot be expanded in vitro, leading to a lack of substantial numbers of human CMs for relevant experimental studies. Almost all cardiac-toxicological tests and experimental studies of drugs for heart disease are performed using animals or primary animal CMs. Owing to their physiological differences between human CMs and CMs from other animals, the accuracy of predicting a drug's effects on human using animals or their CMs is only about 60%. Thus, there are needs of improvement to the existing methods for heart related analysis in drug development. Human CMs derived from stem cells or trans-differentiation provide a tool for cardiac-toxicological analysis. The PSC derived human CMs can be used to establish methods for toxicological analysis at the cellular level. It not only improves the accuracy of the analysis, but also reduces the usage of animals. This approach is currently under extensively research in the bio-pharmaceutical industry. Relevant international regulations and provisions (ICH S7B) for drug registration require cardiac-toxicological analysis to assess the effects of tested drugs on the ventricle, especially the ventricular heart rhythm. Therefore, among the three types of CMs, VM is the most important subtype of CMs for the development of new methods for cardiac-toxicological analysis using human CMs. See, Hartung T, Toxicology for the twenty-first century, *Nature*, 2009, 460:208-212.

In summary, there is a need to generate highly homogeneous stem cell-derived human VMs for either cell transplantation therapy of myocardial infarction or cardiac-toxicological analysis. Therefore, revealing the regulatory mechanisms underlying differentiation of cardiac progenitor cells (CPCs) into VMs has significant implications for the generation of highly homogeneous VMs.

Previously reported methods for cardiac differentiation of stem cells have several drawbacks. The main issues are that the efficiency of cardiac differentiation is low, and the resulting CMs are a heterogeneous population of mixed nodal cells, AMs, and VMs. See, He J Q et al., *Circ Res.* 2003, 93:32-39. In 2007, Murry et al. used a monolayer culture of human ESCs to directly induce cardiac differentiation. The mean differentiation efficiency of the CMs was about 30%. See, Laflamme M A et al., Cardiomyocytes derived from human embryonic stem cells in pro-survival factors enhance function of infarcted rat hearts, *Nat Biotechnol,* 2007, 25:1015-1024, the content of which is incorporated herein by reference in its entirety. After separation and purification by density gradient centrifugation, the resulting CM population was approximately 80% in purity. In 2008, Keller et al. performed suspension culture to form embryoid bodies and then isolated CPCs at day 6 of differentiation by fluorescence-activated cell sorting. With continuous culture and differentiation of these progenitor cells, the cardiac differentiation efficiency was significantly improved, and reached up to 50%. See, Yang L et al., Human cardiovascular progenitor cells develop from a kdr+ embryonic-stem-cell-derived population, *Nature,* 2008, 453:524-528, the content of which is incorporated herein by reference in its entirety. However, none of the above methods can directly differentiate PSCs into highly homogeneous AMs or VMs. In summary, these methods do not facilitate the directed differentiation of AMs or VMs, and the cardiomyocytes population obtained using these methods is a mixture of all three types of CMs. At this point, there has been no relevant study on methods to specifically differentiate each of the three subtypes of CMs. In 2007, a study employed lentiviral transfection of human ESCs to establish a cell line expressing enhanced green fluorescent protein under the control of the conserved promoter of ventricle-specific myosin light chain 2v (MLC-2v) gene. This facilitated the purification of VMs and achieved a purity greater than 90%. However, this method requires insertion of a transgene into the genome of stem cells, and these transgenic CMs are unsuitable for clinical transplantation applications. In 2010, Ma et al. discovered that, during the middle stage of cardiac differentiation of stem cells, i.e., the period during which mesodermal cells convert to CMs (the early stage of cardiac differentiation refers to the stage of differentiation from PSCs to mesodermal cells), retinoic acid treatment induces differentiation of stem cells into AMs. At the same time, inhibition of the retinoic acid pathway effectively induces the cells to differentiate into VMs. See, Zhang Q et al., Direct differentiation of atrial and ventricular myocytes from human embryonic stem cells by alternating retinoid signals, *Cell Res.,* 2011, 21:579-587, the content of which is incorporated herein by reference in its entirety. However, the active regulators in the induction of ventricular differentiation remain unknown.

DESCRIPTION

In one aspect, the objective of the present invention is to provide methods to induce differentiation of PSCs into VMs in vitro.

To achieve this objective, in certain embodiments, the proposed method induces differentiation of PSCs into VMs by treating PSCs in vitro with factors that directly or indirectly activate the Smad1/5/8 signaling pathway during the middle stage of cardiac differentiation of PSCs, thereby achieving directed differentiation towards VMs. Here, in certain embodiments, activation of the Smad1/5/8 signaling pathway includes phosphorylation of one or more Smad proteins in the cytoplasm, including Smad1, Smad5, and Smad8. In certain embodiments, the middle stage of cardiac differentiation refers to the differentiation stage from mesodermal cells or cardiac progenitor cells to CMs. Specifically, in certain embodiments, this stage is initiated by expression of Brachyury (T) and/or Mesp1 genes, and ends before the differentiation of CMs capable of spontaneous contraction.

In any of the preceding embodiments, PSCs can include embryonic stem cells (ESC), induced pluripotent stem cells (iPSCs), embryonic germ cells, or adult stem cells. In any of the preceding embodiments, these cells can be from human or an animal.

In any of the preceding embodiments, the factors that directly or indirectly activate the Smad1/5/8 signaling pathway can be a bone morphogenetic protein, such as BMP 2 and/or BMP4 applied at a final concentration of between about 0.01 and about 1200 ng/mL.

In any of the preceding embodiments, the method can comprise adding one or more factors that promote differentiation of CMs during the early stage of cardiac differentiation of PSCs, namely the stage when PSCs differentiate into mesodermal or cardiac progenitor cells. In some embodiments, the factors that promote differentiation of CMs can include at least one of the following: BMP4, basic fibroblast growth factor (bFGF), activin A, noggin, dorsomorphin, and 6-bromoindirubin-3'-oxime (BIO), or a combination thereof. In any of the preceding embodiments, one or more growth factors can be added to the culture medium at a final concentration ranging from about 0.01 to about 1200 ng/mL. In any of the preceding embodiments, one or more small molecules can be added at a final concentration ranging from about 0.001 to about 100 µM.

In any of the preceding embodiments, one or more inhibitors of the Wnt signaling pathway can also be added to the culture medium during the middle stage of the cardiac differentiation. In any of the preceding embodiments, the Wnt inhibitors can include at least one of the following: dickkopf homolog 1 (DKK1), inhibitor of Wnt production (IWP), and inhibitor of Wnt response (IWR), or a combination thereof. In any of the preceding embodiments, the inhibitor can be added at a final concentration of about 0.001 to about 100 µM. In any of the preceding embodiments, DKK1 can be added with a final concentration from about 0.01 to about 1200 ng/mL.

In any of the preceding embodiments, one or more other regulatory molecules can also be added during the middle stage of cardiac differentiation, including: i) activator of retinoic acid receptor (RARγ) to culture medium without retinoic acid or its precursors; and ii) antagonists of RARα and/or RARβ to culture medium containing retinoic acid or its precursors. In any of the preceding embodiments, the final concentration of the regulatory molecule can be from about 0.001 to about 100 µM.

In some aspects, the present invention provides three technical solutions.

Technical Solution I:

(1) Suspension or monolayer culture of undifferentiated PSCs.

(2) To initiate the cardiac differentiation, adding one or more cytokines (e.g., BMP4, bFGF, activin A, and noggin) that promote differentiation of CMs; and/or adding small molecule inhibitors (e.g., dorsomorphin) of the BMP pathway; and/or adding small molecules (e.g., BIO and CHIR99021) that activate Wnt3a signal pathway to the culture.

(3) During the middle stage of cardiac differentiation, adding one or more growth factors and/or small molecules (e.g., DKK1, IWP, and IWR) that inhibit the Wnt signaling pathway; and/or adding one or more signaling molecules (e.g., BMP2 and/or BMP4) that activate Smad1/5/8 phosphorylation to the culture medium, to induce directed differentiation of cells into VMs. In some embodiments, the inhibitor of the Wnt signaling pathway and the activator of Smad1/5/8 phosphorylation are added substantially simultaneously.

Technical Solution II:

(1) Suspension or monolayer culture of undifferentiated PSCs.

(2) To initiate the cardiac differentiation, adding one or more cytokines (e.g., BMP4, bFGF, activin A, and noggin) that promote differentiation of CMs; and/or adding one or more small molecule inhibitors (e.g., dorsomorphin) of the BMP signaling pathway; and/or adding one or more small molecules (e.g., BIO) capable of activating Wnt3a signal pathway to the culture.

(3) During the middle stage of cardiac differentiation, adding one or more growth factors or small molecules (e.g., DKK1, IWP, and IWR) to the culture medium to inhibit the Wnt signaling pathway; and/or adding one or more factors that can activate cellular expression and secretion of signaling molecules which activate Smad1/5/8 phosphorylation. For example, a RARγ activator (e.g., BMS961) can be added to the culture medium without retinoic acid or its precursors or substrates (e.g., vitamin A). These steps induce directed differentiation of stem cells into VMs.

Technical Solution III:

(1) Suspension or monolayer culture of substantially undifferentiated PSCs.

(2) To initiate the cardiac differentiation, adding one or more cytokines (e.g., BMP4, bFGF, activin A, and noggin) that promote differentiation of CMs; and/or adding one or more small molecule inhibitors (e.g., dorsomorphin) of the BMP pathway; and/or adding one or more small molecules (e.g., BIO) that activate Wnt3a signal pathway to the culture.

(3) During the middle stage of cardiac differentiation, adding one or more growth factors or small molecules (e.g., DKK1, IWP, and IWR) to the culture medium to inhibit the Wnt signaling pathway; and/or adding one or more antagonists of RARα and/or RARβ (e.g., Ro41-5253 for RARα and LE135 for RARβ) to the culture medium containing retinoic acid or its precursors. These steps induce directed differentiation of stem cell-derived CMs mainly into VMs.

In some embodiments, from about day 14 of differentiation, growth factor-free medium is used and replaced every 3 days. After about 60 to about 90 days of differentiation, the percentage of VMs in the differentiated CMs was determined with the analysis of APs of CMs (recorded by the patch clamp technique), calcium imagining studies, and/or MLC-2v and cardiac troponin T (cTNT) double immunofluorescence staining for flow cytometric analysis.

In some embodiments, the present invention enables the application of VMs prepared using a method of any of the preceding embodiments to the cardiac-toxicological analysis and drug screening for heart diseases.

In some embodiments, the present invention enables the application of VMs as prepared using a method of any of the preceding embodiments to stem cell therapy to repair damaged heart tissue.

In other embodiments, the present invention provides methods to promote stem cell differentiation into VMs. In some aspects, the method includes activation of the Smad1/5/8 signaling pathway in mesodermal cells that are derived from stem cells.

In any of the preceding embodiments, the stem cells can include totipotent stem cells, pluripotent stem cells, multipotent stem cells, oligopotent stem cells, and/or unipotent stem cells.

In any of the preceding embodiments, the stem cells can include ESCs, iPSCs, fetal stem cells, and/or adult stem cells.

In any of the preceding embodiments, the stem cells can include mammalian stem cells.

In any of the preceding embodiments, the stem cells can include human stem cells.

In any of the preceding embodiments, the stem cells can include human ESCs and/or iPSCs.

In any of the preceding embodiments, the stem cell differentiation into mesodermal cells can be induced by treating undifferentiated stem cells with at least one of the following: bFGF, BMP2, BMP4, activin A, a BMP antagonist, a BMP signaling pathway inhibitor, or a Wnt3a signaling pathway activator, or a combination thereof.

In any of the preceding embodiments, the BMP antagonist can be a BMP4 antagonist. In any of the preceding embodiments, the BMP antagonist can be noggin.

In any of the preceding embodiments, the BMP signaling pathway inhibitor can be a small molecule inhibitor of the BMP signaling pathway.

In any of the preceding embodiments, the small molecule inhibitor of the BMP signaling pathway can be dorsomorphin.

In any of the preceding embodiments, the Wnt3a signal pathway activator can be a small molecule activator of the Wnt3a signaling pathway.

In any of the preceding embodiments, the small molecule activator of the Wnt3a signaling pathway can be an ATP-competitive inhibitor of GSK-3α/β.

In any of the preceding embodiments, the ATP-competitive inhibitor of GSK-3α/β can be a cell-permeable bis-indolo (indirubin) compound.

In any of the preceding embodiments, the cell-permeable bis-indolo (indirubin) compound can be BIO.

In any of the preceding embodiments, bFGF, BMP2, BMP4, activin A, the BMP antagonist, the BMP signaling pathway inhibitor, and/or the Wnt3a signaling pathway activator, are added at a final concentration of about 0.01 to about 1200 ng/mL, whereas other factors can be added at a final concentration of about 0.001 to about 100 μM.

In any of the preceding embodiments, the stem cells can be treated with BMP2 and/or BMP4 to activate the Smad1/5/8 signaling pathway.

In any of the preceding embodiments, BMP2 and/or BMP4 can be applied at a final concentration of between about 0.01 and about 1200 ng/mL.

In any of the preceding embodiments, the stem cells can be cultured in a medium without retinoic acid or its precursors and treated with a RARγ activator to activate the Smad1/5/8 signaling pathway.

In any of the preceding embodiments, the precursor of retinoic acid can be vitamin A.

In any of the preceding embodiments, the RARγ activator can comprise BMS961, palovarotene, and/or CD437 (e.g., purchased from Sigma-Aldrich).

In any of the preceding embodiments, the RARγ activator can be applied at a final concentration of about 0.001 to about 100 μM.

In any of the preceding embodiments, the stem cells can be treated with one or more RARα and/or RARβ antagonists to activate the Smad1/5/8 signaling pathway.

In any of the preceding embodiments, the RARα antagonist can be Ro41-5253, BMS195614, or ER50891, and the RARβ antagonist can be LE135.

In any of the preceding embodiments, the antagonist of RARα and/or RARβ can be applied at a final concentration of about 0.001 to about 100 μM.

In any of the preceding embodiments, the stem cells can be treated further with a Wnt inhibitor to induce differentiation into VMs.

In any of the preceding embodiments, the Wnt inhibitor can be at least one of the following: DKK1, IWP, or IWR.

In any of the preceding embodiments, the Wnt inhibitor DKK1 can be used at a final concentration of about 0.01 to about 1200 ng/mL, while other inhibitors can be used at about 0.001 to about 100 μM.

In some aspects, the present invention discloses VMs generated by following the method in any of the preceding embodiments.

In any of the preceding embodiments, the VMs can have increased levels or ratios of ventricular-specific gene expression, embryonic ventricular-like APs, and/or the representative characteristic of VMs specific $Ca^{2+}$ activity (e.g., $Ca^{2+}$ spark).

In any of the preceding embodiments, the ventricle-specific gene can be Iroquois homeobox gene 4 (IRX-4) and/or MLC-2v.

In other embodiments, the present invention provides a composition containing stem cells that have differentiated into mesodermal cells and have been treated with an exogenous factor capable of activating the Smad1/5/8 signaling pathway in stem cells.

In any of the preceding embodiments, the exogenous factor that activates the Smad1/5/8 signaling pathway in stem cells can be BMP2 and/or BMP4.

In any of the preceding embodiments, the exogenous factor that activates the Smad1/5/8 signaling pathway in stem cells can be a RARγ activator.

In any of the preceding embodiments, the exogenous factor that activates the Smad1/5/8 signaling pathway in stem cells can be a RARα and/or RARβ antagonist.

In yet other embodiments, the present invention provides a method of deriving VMs from stem cells, which method comprises: 1) treating stem cells with bFGF and BMP4 to induce differentiation; 2) exposing bFGF and BMP4-treated stem cells to activin A to induce mesodermal cells; 3) treating stem cells that have been differentiated into mesoderm cells with noggin to improve the efficiency of stem cell differentiation towards CMs; 4) activating the Smad1/5/8 signaling pathway in noggin-treated stem cells to promote the differentiation of VMs; and 5) exposing noggin-treated stem cells to one or more factors to induce stem cell differentiation into VMs. In some aspects, the one or more factors comprise at least one of the following: DKK1, IWP, and IWR.

In any of the preceding embodiments, the stem cells can be treated with BMP2 and/or BMP4 to activate the Smad1/5/8 signaling pathway.

In any of the preceding embodiments, the stem cells can be cultured in medium without retinoic acid or its precursor, vitamin A, and the cultured cells can be treated with one or more RARγ activators to increase BMP2/4 expression levels to activate the Smad1/5/8 signaling pathway.

In any of the preceding embodiments, the stem cells can be treated with RARα and/or RARβ antagonists to activate the Smad1/5/8 signaling pathway.

In other aspects, the present invention discloses VMs generated by the method in any of the preceding embodiments.

In some aspects, the present invention provides a pharmaceutical composition for treating a subject in need thereof, for example, a subject with heart damage or disease, which composition comprising, consisting essentially of, or consisting of an effective amount of the VMs according to any of the preceding embodiments, and a pharmaceutically acceptable carrier or excipient. In some aspects, provided herein is a method comprising administering to a subject in need thereof an effective amount of the pharmaceutical composition according to any of the preceding embodiments. In some aspects, provided herein is a method comprising administering to a subject in need thereof an effective amount of the VMs according to any of the preceding embodiments.

In any of the preceding embodiments, the subject can be a human.

In any of the preceding embodiments, the method can be used in a stem cell therapy of a heart damage, disease, or condition.

In some embodiments, the present invention provides the use of the VMs according to any of the preceding embodiments for the preparation or manufacture of a medicament for the treatment and/or prevention of a heart damage, disease, or condition.

In some embodiments, the present invention also provides the use of the VMs according to any of the preceding embodiments for screening and/or developing drugs for the treatment and/or prevention of a heart damage, disease, or condition.

In other embodiments, the present invention provides the use of the VMs according to any of the preceding embodiments for cardiac-toxicological analysis for drug safety.

In still other embodiments, the present invention provides a method to identify regulators of VMs by a) treating a VM according to any of the preceding embodiments with one or more candidate regulators and determining the effect of the candidate regulator on the function of VM, and 2) determining the function of VM without treatment with the candidate regulator. If the function of the VM treated with the candidate regulator differs from that of the VM without treatment with the candidate regulator, the candidate regulator is identified as a functional regulator of VMs.

In some embodiments, the present invention provides a method to induce differentiation of PSCs into VMs in vitro. In some aspects, based on direct induction of stem cells, factors (e.g., BMP2 and/or BMP4) that can activate the Smad1/5/8 signaling pathway are directly added to the culture system during the middle stage of cardiac differentiation, thereby directing differentiation of stem cells into CMs. In some aspects, the CMs are mainly VMs. In the culture system containing retinoic acid or its precursors (e.g., vitamin A), addition of factor(s) (e.g., BMP2 and/or BMP4) capable of activating the Smad1/5/8 signaling pathway can effectively inhibit the differentiation of CPCs to AMs while inducing the differentiation towards VMs. In some embodiments, when retinoic acid or vitamin A are added simultaneously with such factor(s) (e.g., BMP2 and/or BMP4) capable of activating the Smad1/5/8 signaling pathway, the proportion of AMs among differentiated CMs decreases with increasing concentrations of BMP4, whereas the proportion of VMs among differentiated CMs increases with increasing BMP4 concentrations. In some aspects, when BMP2/4 only is added during the middle stage of cardiac differentiation when retinoic acid or its precursors are omitted from the culture medium, cardiac progenitor cells efficiently undergo directed differentiation into VMs. In some aspects, during the middle stage of cardiac differentiation of stem cells, addition of an activator of RARα or RARβ to the culture medium effectively inhibits the differentiation of VMs, as reflected by the inhibition of ventricle-specific expression of the early marker gene IRX-4. In some aspects, in the absence of retinoic acid or its precursor vitamin A, addition of a RARγ activator effectively induces stem cell differentiation into VMs. In some aspects, in culture medium containing retinoic acid or vitamin A, addition of RARα and RARβ antagonists is effective to improve the IRX-4 expression level and induce stem cell differentiation into VMs.

In some aspects, the present invention illustrates that BMP and Smad1/5/8 pathways positively regulate differentiation of VMs during the middle stage of cardiac differentiation of stem cells. In some aspects, the present invention allows the generation of highly homogeneous VMs with a desirable biological activity or function.

In some aspects, as an advantage, the present invention does not require any purification steps. In some other aspects, the present invention provides a platform to reveal the regulatory mechanisms underlying differentiation of cardiac progenitor cells to VMs. In still other aspects, the present invention has significant implications for cell transplantation therapy of myocardial infarction as well as drug research and development using human stem cell-derived CMs.

DESCRIPTION OF DRAWINGS

FIG. 1A shows reverse transcription-polymerase chain reaction (RT-PCR) analysis of the expression of BMP2, BMP4, and their receptors at 5 and 6 days of cardiac differentiation. FIG. 1B shows western blot analysis of downstream signaling molecules [phosphorylated Smad1/5/8 (P-Smad1/5/8)] of the BMP pathway. T-Smad1/5/8 represents total Smad1/5/8 proteins. β-actin served as an internal loading control. The histogram in FIG. 1C presents the experimental results of quantitative RT-PCR analysis of IRX-4 gene expression levels at 14 days of differentiation. The results show IRX-4 expression levels in cells treated with 1 μM retinoic acid and 200 ng/mL BMP4 during different stages of differentiation. Connected line indicates the cardiac differentiation efficiency of the stem cells under the corresponding inductive conditions. N represents noggin, B represents BMP4; NVa represents differentiated cells cultured in vitamin A-free medium; RA represents retinoic acid; and numbers represent the concentrations (Unit for BMP4 is ng/mL). Data are expressed as relative values compared with the expression level of glyceraldehyde-3-phosphate dehydrogenase (GADPH).

FIG. 2A shows that, after the addition of BMP4 with various concentrations to the cultures, the IRX-4 expression level is elevated with increasing concentrations of BMP4. However, the expression level is reduced by addition of a BMP antagonist, noggin. FIG. 2B illustrates that the IRX-4 expression level is effectively reduced by addition of various doses of noggin to the medium without the retinoic acid precursor, vitamin A. FIG. 2C shows that in the presence of 1 μM retinoic acid, the IRX-4 expression level is elevated with increasing concentrations of BMP4 added to the cultures. FIG. 2D shows that the elevation of the IRX-4 expression level by BMP4 in the presence of retinoic acid is reduced with additions of increasing concentrations of noggin in the cultures. N represents noggin; B represents BMP4, NVa represents differentiated cells treated in vitamin A-free medium; RA represents retinoic acid; and numbers represents the concentrations (Unit is ng/mL). The results of quantitative RT-PCR are indicated as relative values compared with the expression levels of GADPH.

FIG. 4A shows western blot analysis of MLC-2v expression in stem cell-derived CMs at day 90 of differentiation treated with retinoic acid, noggin and BMP4 with different combinations. FIG. 4B presents the results of double immunofluorescence staining of cTNT and MLC-2v in CMs at day 90 of differentiation after retinoic acid, BMP4, and noggin treatments. Letter B in the figures represents BMP4, NVa represents differentiated cells cultured in vitamin A-free medium; RA represents 1 μM retinoic acid; and numbers represent the concentrations (ng/mL).

FIG. 5A shows the features of $Ca^{2+}$ sparks in CMs with ventricular-like APs, $Ca^{2+}$ transients in cells with atrial-like APs, and $Ca^{2+}$ oscillations in cells with nodal-like APs. FIG. 5B presents the proportions of CMs with $Ca^{2+}$ sparks, $Ca^{2+}$ transients, and $Ca^{2+}$ oscillations in different treatments as classified by calcium signaling patterns of the various subtypes of CMs in A. The vertical axis represents the proportions of CMs with the three different calcium activities; RA represents 1 μM retinoic acid; Letter B represents BMP4; NVa represents vitamin A-free medium; N represents noggin; and numbers represent the concentrations (ng/mL).

FIG. 8A shows the proportion of cells with atrial-, ventricular-, and nodal-like APs in CMs differentiated under various induction conditions (n>30). FIG. 8B shows flow cytometric analyses of the proportions of MLC-2v-expressing cells in the total cardiomyocytes population (cTNT-positive cells) among 90 day cultures treated under various conditions. RA represents 1 μM retinoic acid; B represents BMP4; NVa represents vitamin A-free medium; N represents noggin; and numbers represent the concentrations (Unit is ng/mL). The RARγ concentration is 0.1 μM.

In FIGS. 12-17, "*" indicates non-ventricular CMs and "^" indicates MLC-2v-expressing VMs.

EXAMPLES

The following examples are provided to describe the present invention, but do not restrict the scope of the present invention. Unless specified otherwise, the technical terms used in the embodiments are conventional terms known to those individuals skilled in the procedures using materials that are commercially available.

In the following examples, the human ESC line H7 was purchased from WiCell Research Institute, USA; B27 supplement and RPMI1640 medium were purchased from Invitrogen; Activin A, bFGF, DKK1, BMP4, and noggin were purchased from R&D systems.

Example 1

Figure 1:
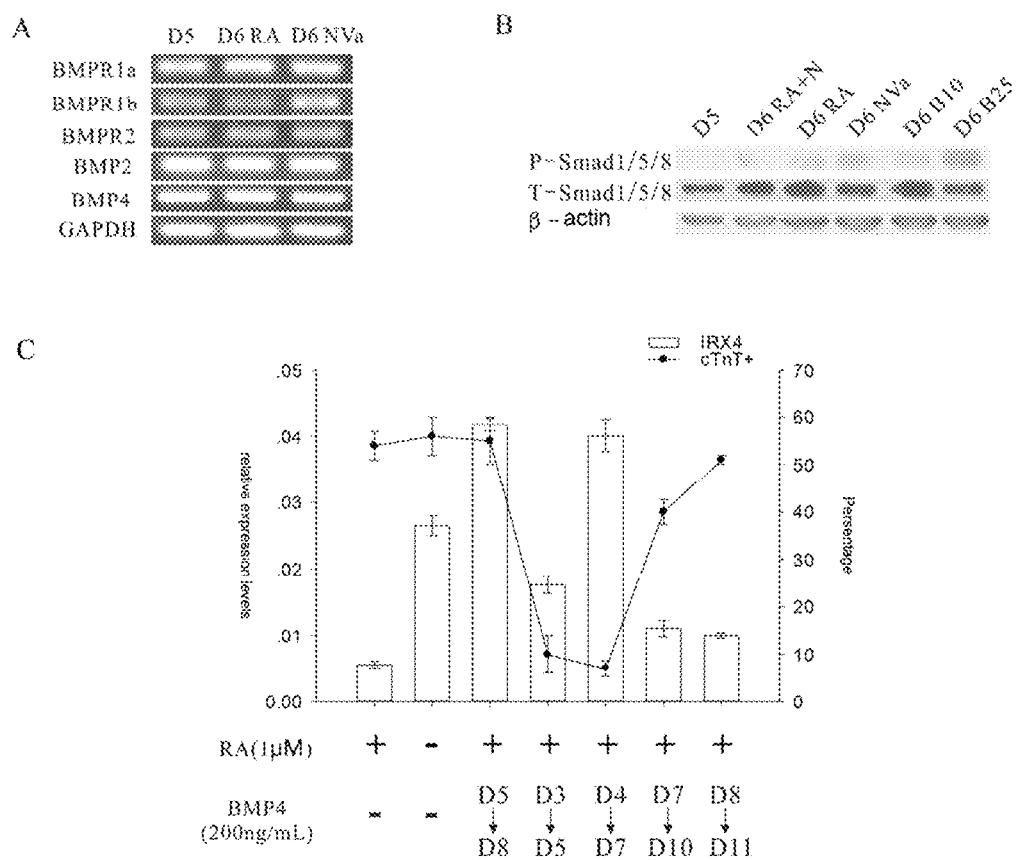
FIG. 1 shows the expression of molecules involved in the BMP signaling pathway during the middle stage of cardiac differentiation of stem cells, and the effects on expression of the ventricle-specific marker gene IRX-4.

Role of BMP/Smad1/5/8 Signaling Pathways in Inducing Differentiation of Cardiac Progenitor Cells into VMs 1) Previous research indicated that during cardiac differentiation of stem cells, addition of retinoic acid or its precursors (e.g., vitamin A) to the culture medium at the differentiation stage that determines the subtype of CMs induces directed differentiation of stem cells into AMs. On the other side, addition of a retinoic acid inhibitor to the culture medium or exclusion of vitamin A in the culture medium induces directed differentiation of stem cells into VMs. See, Zhang Q et al., Cell Res., 2011, 21:579-587. Using RT-PCR, the expression of BMP2/4 and their corresponding receptor in differentiated human ESCs was analyzed during the middle stage of cardiac differentiation. As shown in FIG. 1, both the ligands and receptors of the BMP pathway are expressed in the cultured cells. Western blot analysis of BMP2/4 downstream signaling molecules (phosphorylated Smad1/5/8) showed that under the culture condition with retinoic acid addition and in the absence of retinoic acid or vitamin A, Smad1/5/8 molecules are phosphorylated (FIG. 1). These results demonstrated that activation of the BMP pathway during the middle stage of cardiac differentiation of stem cells. These results indicated that during days 5-8 of stem cell differentiation, the BMP pathway is involved in regulating the differentiation of cardiac progenitor cells into VMs.

2) The role of the BMP pathway in directed differentiation of CM subtypes was analyzed further during cardiac differentiation of stem cells. IRX-4 is a marker gene expressed during early differentiation of VMs. Thus, the IRX-4 expression level was measured to further study the role of the BMP pathway in differentiation of CM subtypes.

Figure 2:
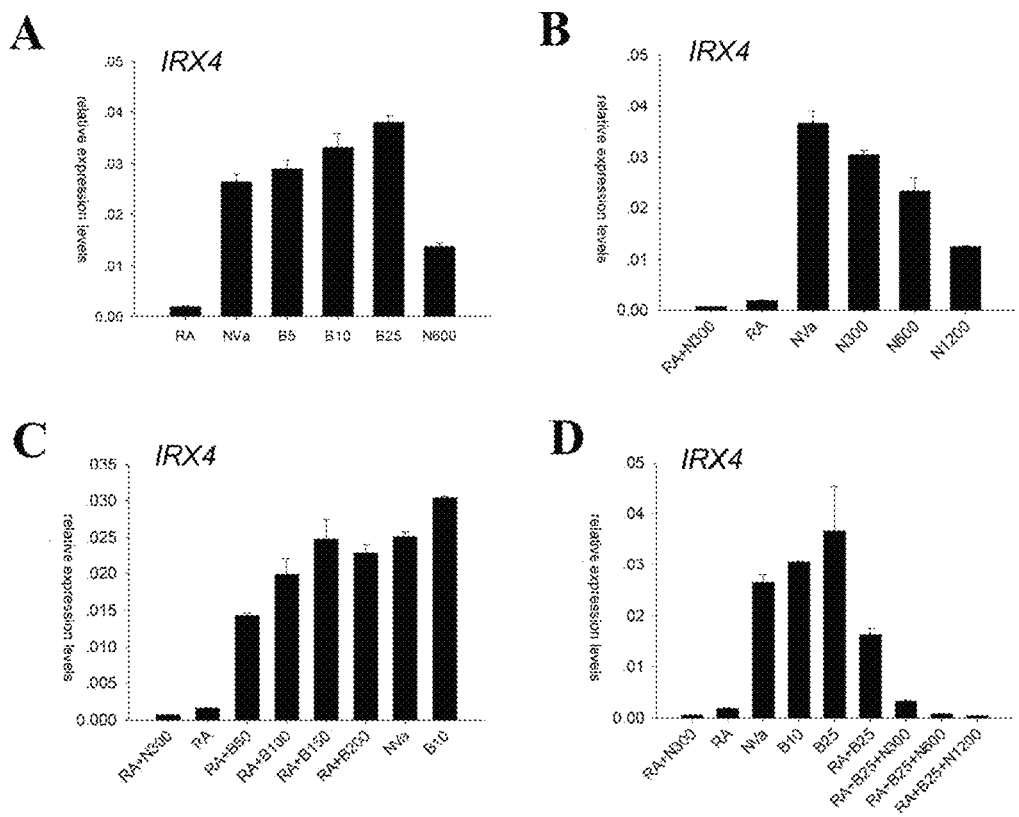
FIG. 2 presents quantitative RT-PCR analysis of the expression levels of the ventricle-specific early marker gene IRX-4 at day 14 in differentiated cultures with various treatments.

As indicated in FIG. 2, in vitamin A-free medium, the IRX-4 expression level was effectively reduced by addition of a BMP2/4 pathway inhibitor, noggin, during day 5 to day 8 of differentiation. The expression level of IRX-4 decreased with increasing doses of noggin (300, 600, and 1200 ng/mL).

3) IRX-4 expression level was repressed by addition of retinoic acid during day 5 to day 8 of differentiation. Furthermore, when retinoic acid was added simultaneously with various doses of BMP4 during day 5 to day 8 of differentiation, and the measurement of the expression levels of IRX-4 by quantitative RT-PCR showed that the IRX-4 expression level in retinoic acid-treated culture was elevated by addition of BMP. As the dose of BMP4 increased, the expression level of IRX-4 increased correspondingly (FIG. 2).

Figure 3:
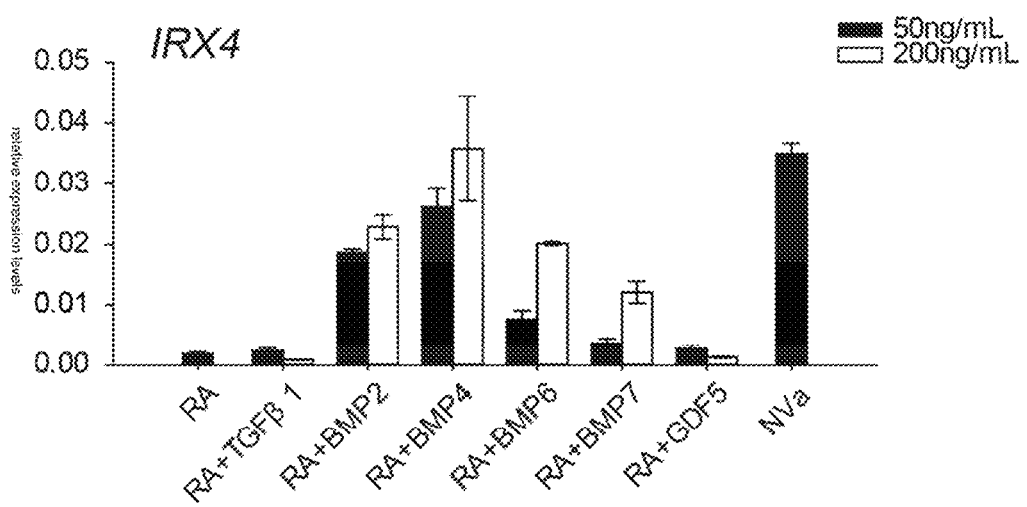
FIG. 3 presents quantitative RT-PCR analysis of IRX-4 gene expression levels at day 14 of differentiation. The results show that by treatment of the stem cells at days 5-8 of cardiac differentiation, other members of the BMP family also effectively antagonized the inhibitory effect of retinoic acid on IRX-4 expression. The antagonistic effect is enhanced with increasing doses of BMP family member growth factors. RA represents retinoic acid; numbers represent the concentrations of the growth factor (Unit is ng/mL); the concentration of retinoic acid is 1 μM. The results of quantitative RT-PCR are indicated as relative values compared with the expression levels of GADPH.

Additionally, other members of the BMP family antagonize the inhibitory effect of retinoic acid on IRX-4 expression. Most BMP family members have similar functions. Quantitative RT-PCR analysis (FIG. 3) showed that during middle stage of cardiac differentiation, the IRX-4 expression level was elevated to various degrees by other BMP family members in the presence of 1 μM retinoic acid. The expression level of IRX-4 increased with increasing concentrations of those BMP family members added to the medium.

In summary, the analysis of early specific IRX-4 expression in differentiated cultures indicated that the BMP signaling pathway effectively improves IRX-4 expression in differentiated CMs. This finding shows that during differentiation of stem cells, the BMP signaling pathway is involved in their early differentiation into VMs and plays a role in promoting this process.

Figure 5:
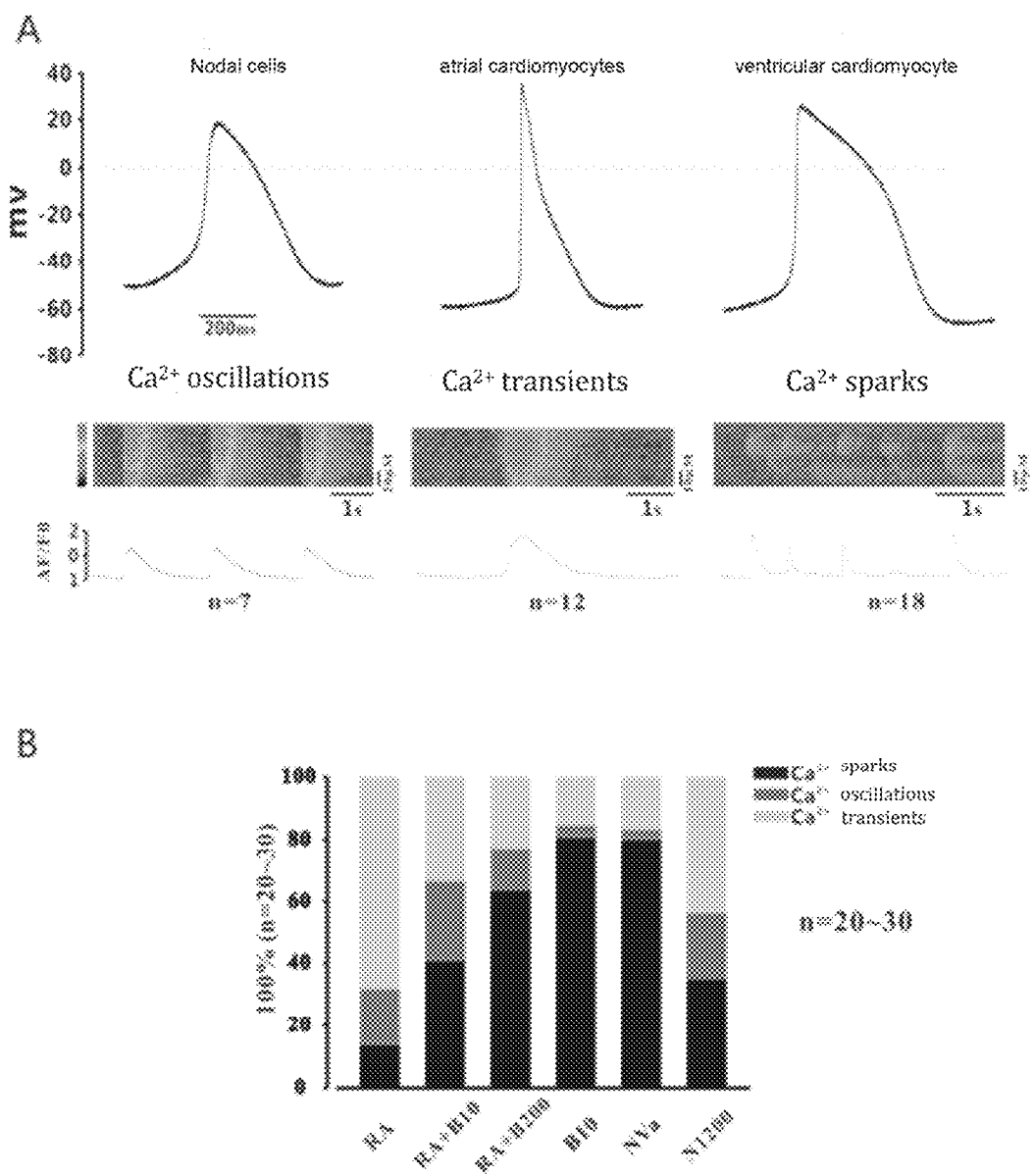
FIG. 5 presents images from confocal laser scanning microscopy and simultaneous recordings of APs of calcium activity in differentiated CMs and the classification of the differentiated CMs according to the specific calcium activity patterns in the various types of CMs.

4) To verify the role of the BMP pathway in regulating the differentiation of VMs from stem cells, calcium activities of cardiomyocytes were recorded with confocal laser scanning microscopy at 60-90 days of differentiation. Calcium activity in VMs clearly differs from that in AMs and nodel cells. Calcium activity in VMs has a higher imaging frequency, known as $Ca^+$ sparks. Imaging of the AM calcium activity showed a lower frequency with large signals, called $Ca^+$ transients, whereas imaging of calcium activity in nodel cells demonstrated obvious periodicity called $Ca^+$ oscillations. First, using the single-cell patch clamp technique in conjunction with confocal laser scanning microscopy, it was found that patch clamp-recorded calcium activities in 20 cells with ventricular-like APs exclusively shows $Ca^+$ sparks. Patch clamp-recorded calcium activities in 20 cells with atrial-like APs exclusively showed $Ca^+$ transients, whereas patch clamp-recorded calcium activities in 20 cells with nodal-like APs exclusively shows $Ca^+$ oscillations. Thus, comparing the image pattern of calcium activities in CMs is an effective method to distinguish VMs from AMs and nodel cells. Calcium imaging data showed that the majority of differentiated CMs with retinoic acid treatment had $Ca^+$ transients, while the proportion of cells with $Ca^+$ transients decreased with increasing concentrations of BMP4. In contrast, the proportion of cells with $Ca^+$ sparks among differentiated CMs increased with increasing concentrations of BMP4. This result indicates that activation of the BMP signaling pathway effectively induces stem cells to differentiate into VMs (FIG. 5).

Figure 4:
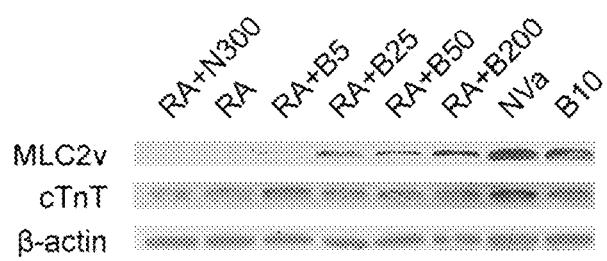
FIG. 4 displays ventricle-specific MLC-2v expression in long term cultures that differently treated with retinoic acid, BMP4, and noggin.
Figure 4:
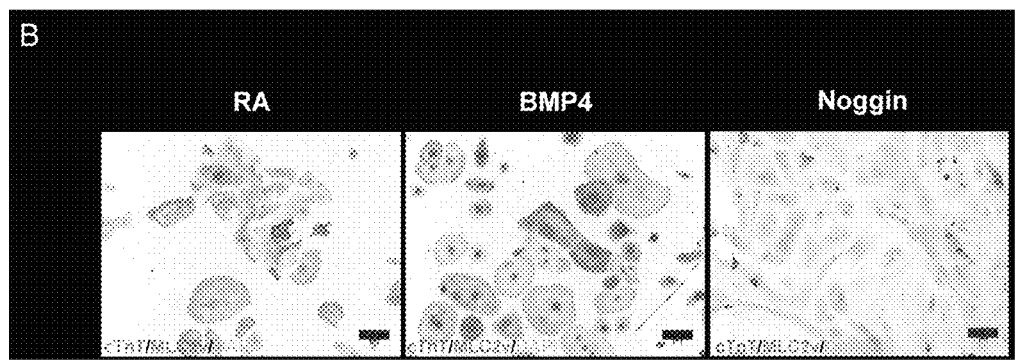
Figure 8:
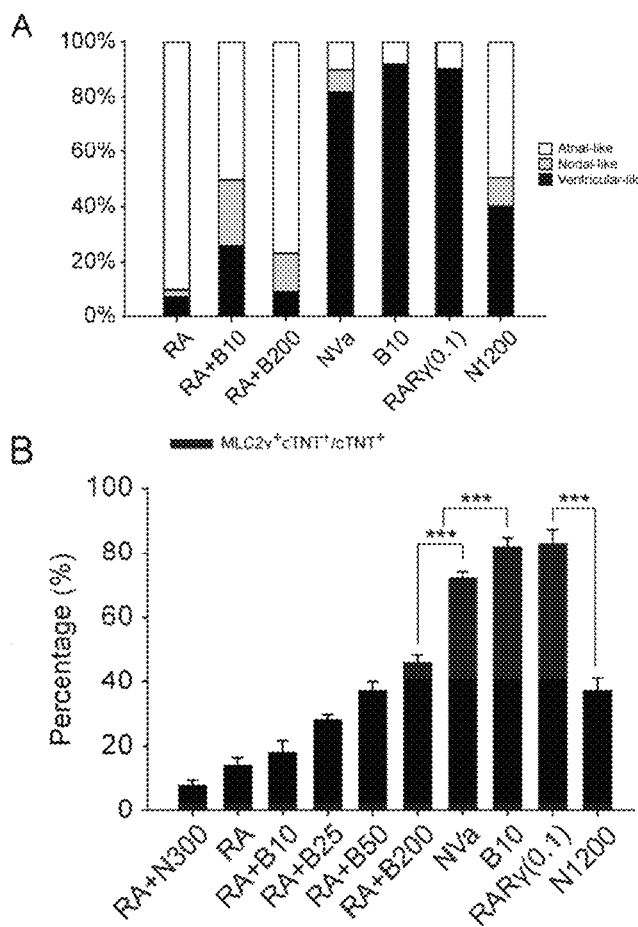
FIG. 8 shows the proportions of cardiomyocytes with different AP characteristics, and MLC-2v (a mature VM-specific marker gene) expressing cells in the total cardiomyocyte population differentiated under various differentiation conditions.

5) As mentioned above, during early differentiation of CMs, IRX-4 is an important gene with specific expression in differentiated VMs. As CMs mature, VMs begin to specifically express the MLC-2v gene. Thus, the MLC-2v expression level was measured in differentiated cells at day 90 of culture after treatment with various growth factors. Western blot analysis showed that the MLC-2v protein expression level in differentiated cells at day 90 also increased with increasing concentrations of BMP4 (FIG. 4). Moreover, flow cytometry was performed to determine the proportion of MLC-2v-expressing VMs among differentiated CMs (cTNT-expressing cells) at day 90. The results (FIG. 8) showed that addition of BMP4 to differentiated cells after retinoic acid treatment effectively increased the proportion of MLC-2v-expressing cells among differentiated CMs, with the highest proportion obtained by BMP4 treatment alone. The most classical method to identify the subtypes of CMs is to measure the APs of the CMs. The proportions of cells with atrial-, ventricular-, and nodal-like APs among differentiated CMs were analyzed after treatment with retinoic acid and various doses of BMP4 (FIG. 8). Among differentiated CMs after retinoic acid treatment, the proportion of cells with ventricular-like APs increased significantly with increasing doses of BMP4. Among differentiated cells treated with BMP4 alone, more than 90% of CMs had ventricular-like APs, indicating that more than 90% of CMs were VMs.

Figure 6:
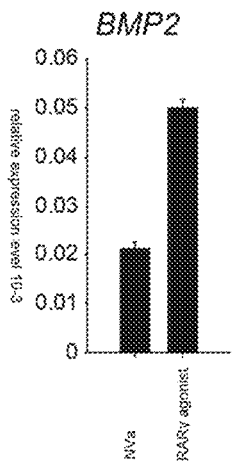
FIG. 6 shows quantitative RT-PCR analysis of BMP2 expression in cells treated with a RARγ activator at day 6 of differentiation. The results of quantitative RT-PCR are indicated as relative values compared with those of GADPH. NVa represents vitamin A-free medium.
Figure 7:
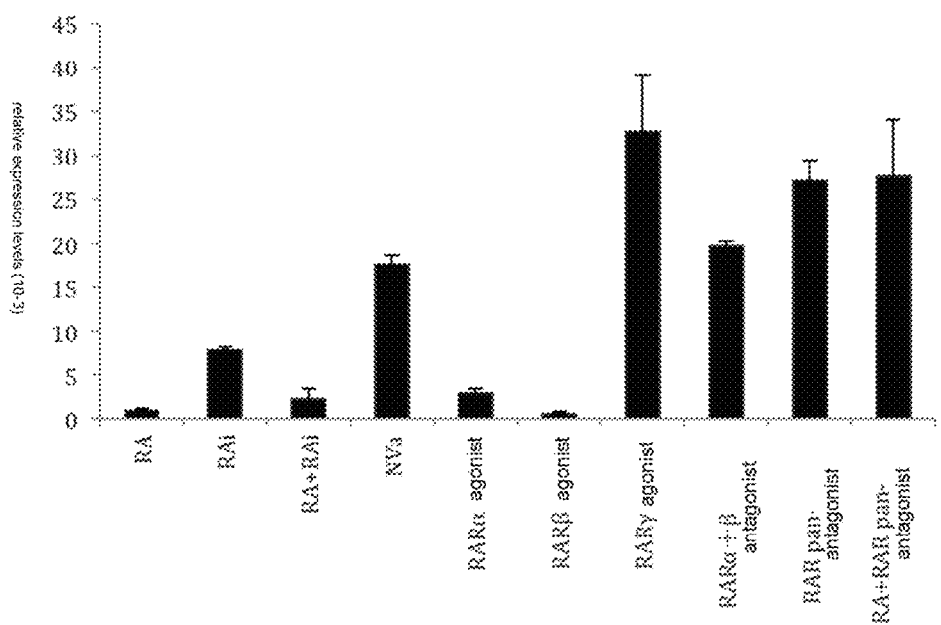
FIG. 7 shows quantitative RT-PCR analysis of ventricle-specific IRX-4 expression at day 14 of stem cell differentiation after the addition of various regulators (a RAR activator or inhibitor) to vitamin A-free medium during middle stage of cardiac differentiation of stem cells. RA represents retinoic acid; RAi represents a retinoic acid inhibitor, BMS189453; NVa represents vitamin A-free medium; The RAR pan-antagonist is BMS493. The results of quantitative RT-PCR are expressed as relative values compared with cTNT expression

6) Addition of BMP2/4, activin A, bFGF and/or noggin during early cardiac differentiation of ESCs and growth factors such as DKK1 during the middle stage of cardiac differentiation efficiently induced stem cells to differentiate into CMs. Quantitative RT-PCR analysis showed that ventricle-specific IRX-4 expression was reduced by addition of RARα and RARβ activators along with DKK1 during middle stage of cardiac differentiation (FIG. 7). However, high expression of BMP2 and IRX-4 was induced by addition of DKK1 with a RARγ activator (FIGS. 6 and 7). Additionally, in vitamin A-containing medium, early specific IRX-4 expression in VMs was activated by addition of DKK1 and antagonists of RARα and RAR. This indicated induced differentiation of stem cells into VMs. Because retinoic acid has three RARs receptors (RARα, RARβ, and RARγ), simultaneous inhibition of RARα and RARβ in the presence of vitamin A or retinoic acid has a similar mechanism and effect as that of independent activation of RARγ alone.

Flow cytometric analysis (FIG. 8) demonstrated that the proportion of MLC-2v-expressing cardiomyocytes in cardiomyocytes population (cTNT-expressing cells) reached up to 80% at 90 days of differentiation induced by RARγ. Additionally, electrophysiological identification of APs indicated that 92% of RARγ-induced, differentiated CMs at 90 days had ventricular-like APs.

Example 2

Inducing Differentiation of PSCs into VMs In Vitro (Technical Solution I)

Figure 9:
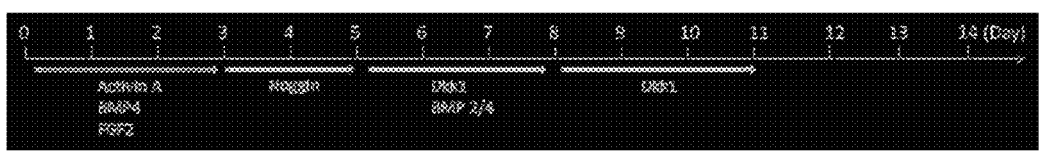
FIG. 9 illustrates the process of inducing differentiation of PSCs into VMs in vitro in Example 2 (infra) of the present invention.

The human ESC line H7 was cultured on gelatin-coated petri dishes in RPMI 1640 medium supplemented with B27 at 37° C. in a $CO_2$ incubator. The process of cardiac differentiation is presented in FIG. 9. During the first 3 days of differentiation, the differentiation medium contained activin A (10 ng/mL), BMP4 (6 ng/mL), and bFGF (6 ng/mL). At the end of day 3, the medium was exchanged with a BMP2/4 inhibitor, noggin (300 ng/mL) added to the medium. At the end of day 5, the medium was replaced with vitamin A-free, B27 supplemented RPMI1640 medium. A Wnt3a inhibitor, DKK1 (300 ng/mL) and BMP4 (10 ng/mL) were also added to the medium. At the end of day 8, the medium was replaced with medium containing 300 ng/mL DKK1 only. At the end of day 10, the medium was replaced with growth factor-free medium. Thereafter, the medium was replaced with B27-containing RPMI1640 medium every 3 days. A large number of beating CMs was observed at day 14 of differentiation. The workflow of the technical solution is shown in FIG. 9.

Example 3

Inducing Differentiation of PSCs into VMs In Vitro (Technical Solution II)

Figure 10:
FIG. 10 illustrates the process of inducing differentiation of PSCs into VMs in vitro in Example 3 (infra) of the present invention.

The human ESC line H7 was cultured on gelatin-coated petri dishes in RPMI 1640 medium with 1×B27 at 37° C. in a $CO_2$ incubator. The process of cardiac differentiation is presented in FIG. 10. During the first 3 days of differentiation, the differentiation medium contained activin A (10 ng/mL), BMP4 (6 ng/mL), and bFGF (6 ng/mL). At the end of day 3, the medium was exchanged with differentiation medium containing a BMP2/4 inhibitor, noggin (300 ng/mL). At the end of day 5, the medium was replaced with vitamin A-free, B27-containing RPMI 1640 medium containing a Wnt3a inhibitor, DKK1 (300 ng/mL), and RARγ activator, BMS961 (0.1 μM, Tocris). At the end of day 8, the medium was replaced with medium containing 300 ng/mL DKK1 only. At the end of day 10, the medium was replaced with growth factor-free medium. Thereafter, the medium was replaced with B27-containing RPMI 1640 medium every 3 days. A large number of beating CMs was observed at day 14 of differentiation. The workflow of the technical solution is shown in FIG. 10.

Example 4

Inducing Differentiation of PSCs into VMs In Vitro (Technical Solution III)

Figure 11:
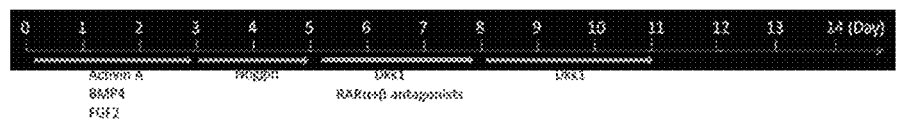
FIG. 11 illustrates the process of inducing differentiation of PSCs into VMs in vitro in Example 4 (infra) of the present invention.

The human ESC line H7 was cultured on gelatin-coated petri dishes in 1×B27-containing RPMI 1640 medium at 37° C. in a $CO_2$ incubator. The process of cardiac differentiation is presented in FIG. 11. During the first 3 days of differentiation, the differentiation medium contained activin A (10 ng/mL), BMP4 (6 ng/mL), and bFGF (6 ng/mL). At the end of day 3, the medium was exchanged with differentiation medium containing a BMP2/4 inhibitor, noggin (300 ng/mL). At the end of day 5, the medium was replaced with vitamin A-free, B27-containing RPMI1640 medium containing a Wnt3a inhibitor, DKK1 (300 ng/mL), as well as antagonists of RARα and RARβ, BMS195614 (0.1 μM) and LE135 (0.5 μM), respectively. At the end of day 8, the medium was replaced with medium containing 300 ng/mL DKK1 only. At the end of day 10, the culture medium was replaced with growth factor-free medium. Thereafter, the medium was replaced with B27-containing RPMI 1640 medium every 3 days. A large number of beating CMs was observed at day 14 of differentiation. The workflow of the technical solution is shown in FIG. 11.

Figure 12:
FIG. 12 presents the results of double immunofluorescence staining of cTnT and MLC-2v in differentiated CMs after retinoic acid treatment.

FIG. 12 shows the results of double immunofluorescence staining of cTnT and MLC-2v in differentiated CMs after retinoic acid treatment.

Figure 13:
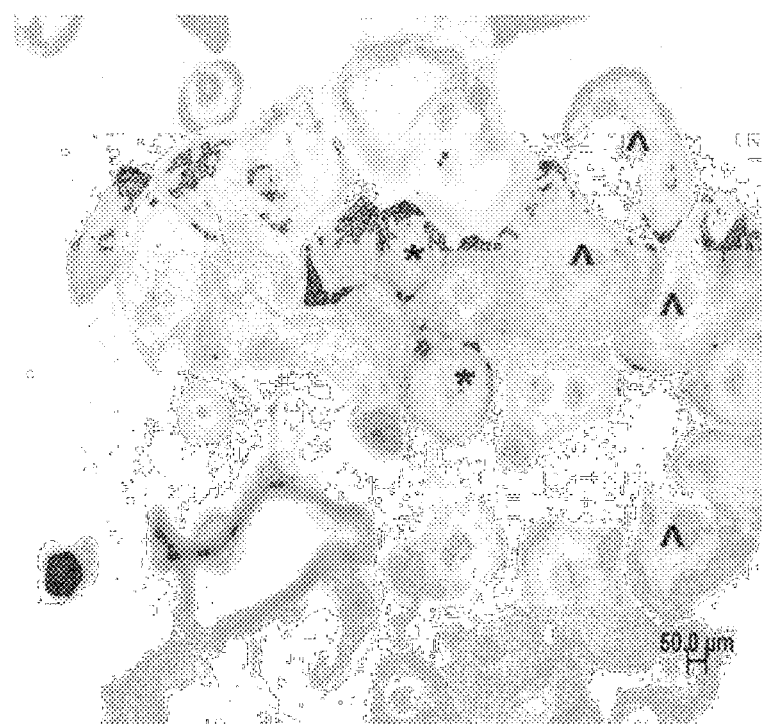
FIG. 13 presents the results of double immunofluorescence staining of cTnT and MLC-2v in differentiated CMs after treatment with retinoic acid and 200 ng/mL BMP4.

FIG. 13 shows the results of double immunofluorescence staining of cTnT and MLC-2v in differentiated CMs after treatment with retinoic acid and 200 ng/mL BMP4.

Figure 14:
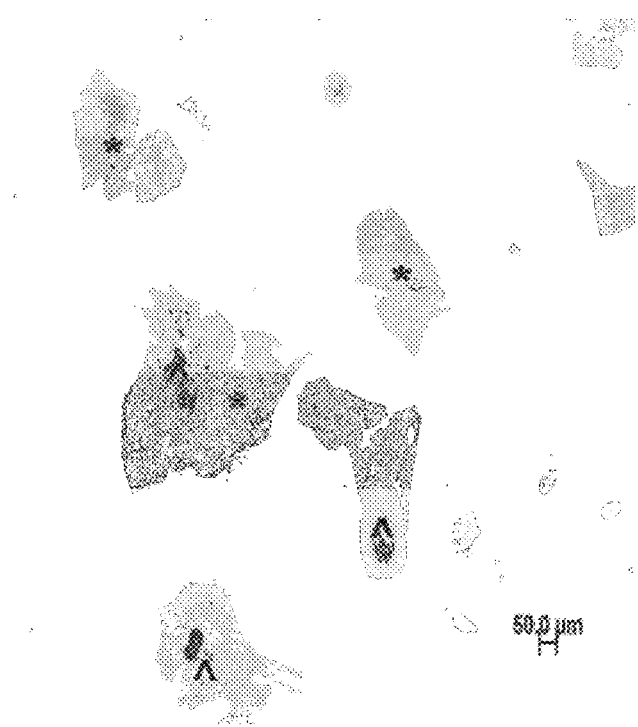
FIG. 14 presents the results of double immunofluorescence staining of cTnT and MLC-2v in differentiated CMs after treatment with 1200 ng/mL noggin in vitamin A-free medium.

FIG. 14 shows the results of double immunofluorescence staining of cTnT and MLC-2v in differentiated CMs after treatment with 1200 ng/mL Noggin in vitamin A-free medium.

Figure 15:
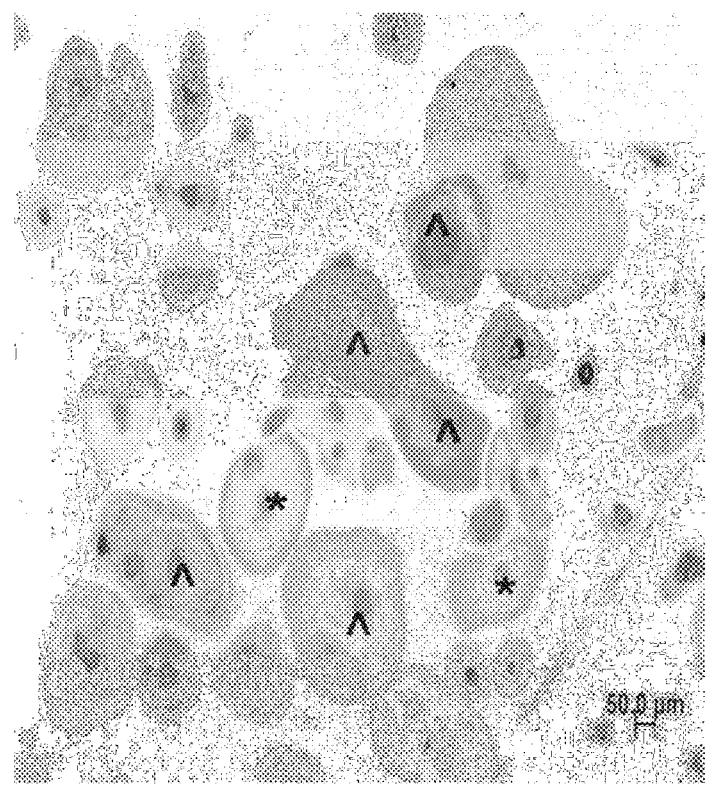
FIG. 15 presents the results of double immunofluorescence staining of cTnT and MLC-2v in differentiated CMs acquired from Example 2 (infra).

FIG. 15 shows the results of double immunofluorescence staining of cTnT and MLC-2v in differentiated CMs acquired from Example 2.

Figure 16:
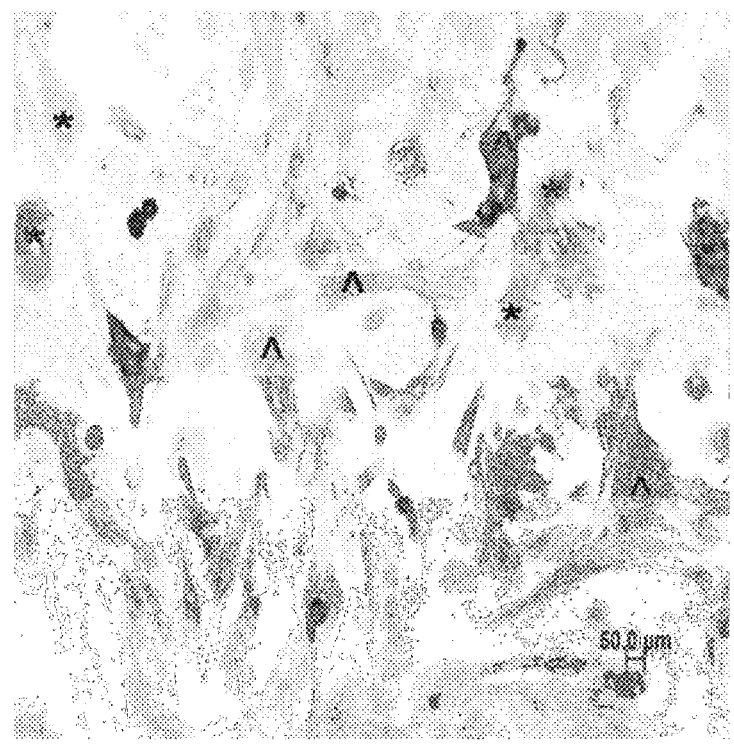
FIG. 16 presents the results of double immunofluorescence staining of cTnT and MLC-2v in differentiated CMs after culture in vitamin A-free medium.

FIG. 16 shows the results of double immunofluorescence staining of cTnT and MLC-2v in differentiated CMs after culture in vitamin A-free medium.

Figure 17:
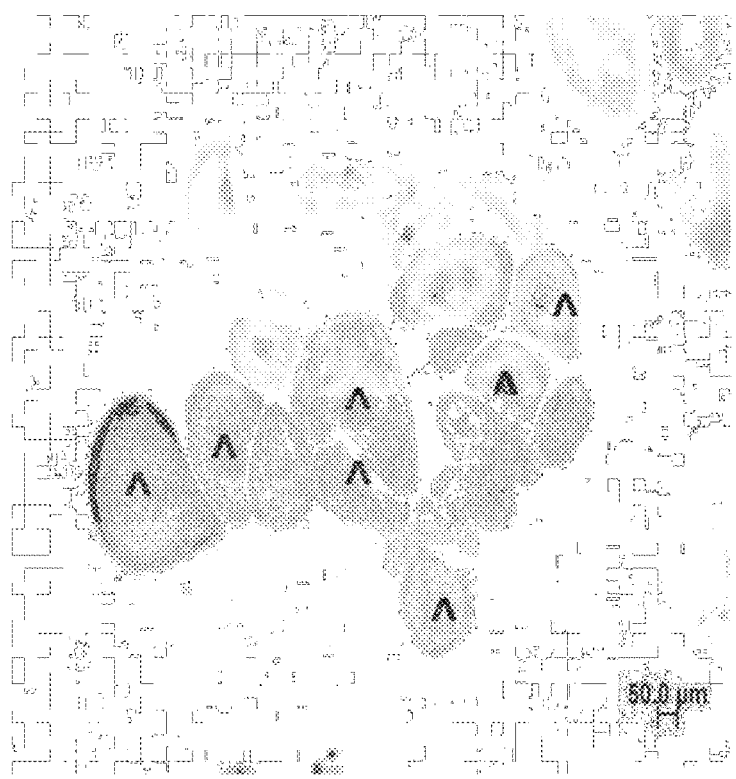
FIG. 17 presents the results of double immunofluorescence staining of cTnT and MLC-2v in differentiated CMs acquired from Example 3 (infra).

FIG. 17 shows the results of double immunofluorescence staining of cTnT and MLC-2v in differentiated CMs acquired from Example 3.

In FIGS. 12-17, "*" indicates non-ventricular CMs and "^" indicates MLC-2v-expressing VMs.

Confocal laser scanning microscopy was performed to analyze calcium activities in differentiated CMs acquired from Example 2 and 3 at 60-90 days. The results of calcium imaging are shown in FIG. 5, from which the proportion of cells with $Ca^{2+}$ sparks among total differentiated CMs can be calculated directly.

In the above examples, the effective ranges of the final concentration for the relevant additives in the medium are 0.01-1200 ng/mL for growth factors and 0.001-100 μM for small molecules.

In some aspects, the methods disclosed in the present invention successfully generate biologically active and functional VMs. These methods can be used to reveal the regulatory mechanisms of CPC differentiation into VMs, whereas the resulting differentiated human VMs have extensive applications in cell transplantation therapy of myocardial infarction, toxicological analysis of cardiac drugs, and cardiac drug development.

Although the present invention has been fully described with general instructions and specific embodiments, it is noted that various changes and modifications will become apparent to those skilled in the procedures. Therefore, such changes and modifications made to the invention without departing from its essence are being protected within the scope of the present invention as claimed.

INDUSTRIAL APPLICABILITY

In some aspects, the present invention provides a method to induce differentiation of PSCs into VMs in vitro, which successfully generates biologically active and functional VMs. It can not only reveal the regulatory mechanisms underlying differentiation of VMs from CSCs, but also produce human VMs that have broad applications in cell transplantation therapy of myocardial infarction, as well as cardiac-toxicological analysis of drug safety, and drug development for heart diseases.

The invention claimed is:
1. A method for promoting stem cell differentiation into a ventricular cardiomyocyte, the method comprising:
   1) activating the Smad1/5/8 signaling pathway in a mesodermal cell or a cardiac progenitor cell that is differentiated from a stem cell; and
   2) inhibiting the Wnt signaling pathway in the mesodermal cell or cardiac progenitor cell, and
   3) without purification, obtaining a cardiomyocyte cell population differentiated from the mesodermal cell or cardiac progenitor cell, wherein at least 80% of the cardiomyocyte population are ventricular cardiomyocytes,
   wherein said mesodermal cell or cardiac progenitor cell is simultaneously contacted with an exogenous activator of the Smad1/5/8 signaling pathway and an exogenous inhibitor of the Wnt signaling pathway in a same cell culture medium, thereby activating said Smad1/5/8 signaling pathway and inhibiting said Wnt signaling pathway in said mesodermal cell or cardiac progenitor cell.

2. The method of claim 1, wherein the stem cell is a pluripotent stem cell, a totipotent stem cell, a multipotent stem cell, an oligopotent stem cell, a unipotent stem cell, an embryonic stem cell, an induced pluripotent stem cell, a fetal stem cell, or an adult stem cell.

3. The method of claim 1, wherein the stem cell is a mammalian stem cell.

4. The method of claim 3, wherein the stem cell is a human stem cell, a human embryonic stem cell, or a human induced pluripotent stem cell.

5. The method of claim 1, wherein the stem cell has differentiated to form the mesodermal cell by contacting the stem cell with one or more of basic fibroblast growth factor (bFGF), bone morphogenetic protein 2 (BMP 2), bone morphogenetic protein 4 (BMP 4), activin A, a BMP antagonist, a BMP pathway inhibitor, and a Wnt3a pathway activator.

6. The method of claim 5, wherein the BMP antagonist is a BMP 4 antagonist, the BMP pathway inhibitor is a small molecule BMP pathway inhibitor, and/or the Wnt3a pathway activator is a small molecule Wnt3a pathway activator.

7. The method of claim 6, wherein the BMP 4 antagonist is Noggin, the small molecule BMP pathway inhibitor is Dorsomorphin, and/or the small molecule Wnt3a pathway activator is an ATP-competitive inhibitor of GSK-3α/β, a cell-permeable bis-indolo (indirubin) compound, or 6-bromoindirubin-3'-oxime (BIO).

8. The method of claim 1, wherein the Smad1/5/8 pathway is activated by:
contacting the mesodermal cell with a BMP family member;
contacting the mesodermal cell with an agonist of retinoic acid receptor γ (RARγ), wherein the mesodermal cell is cultured in a medium that does not comprise retinoic acid or a precursor thereof; or
contacting the mesodermal cell with an antagonist of retinoic acid receptor α (RARα) and/or retinoic acid receptor β (RARβ), wherein the mesodermal cell is cultured in a medium comprising retinoic acid or a precursor thereof.

9. The method of claim 8, wherein:
the BMP family member comprises BMP 2 and/or BMP 4, and the BMP 2 and/or BMP 4 is used at a final concentration of 0.01-1200 ng/ml;
the retinoic acid precursor is vitamin A, and/or the RARγ agonist is BMS961 (3-Fluoro-4-[[2-hydroxy-2-(5,5,8, 8-tetramethyl-5,6,7,8,-tetrahydro-2-naphthalenyl) acetyl]amino]-benzoic acid), Palovarotene (4-[(E)-2-[5,5,8,8-tetramethyl-3-(1H-pyrazol-1-ylmethyl)-5,6,7, 8-tetrahydronaphthalen-2-yl]ethenyl]benzoic acid), or CD 437 (6-(4-Hydroxy-3-tricyclo[3.3.1.13,7]dec-1-ylphenyl)-2-naphthalenecarboxylic acid), and/or the RARγ agonist is used at a final concentration of 0.001-100 μM; or
the antagonist of RARα is Ro41-5253, BMS195614, or ER50891, and/or the antagonist of RARβ is LE135, and/or the antagonist of RARα and/or RARβ is used at a final concentration of 0.001-100 μM.

10. The method of claim 1, wherein the inhibition of the Wnt signaling pathway comprises contacting the mesodermal cell with a Wnt inhibitor to differentiate the mesodermal cell into a ventricular cardiomyocyte.

11. The method of claim 10, wherein the Wnt inhibitor comprises at least one of dickkopf homolog 1 (DKK1), IWP, and an inhibitor of Wnt response (IWR).

12. The method of claim 10, wherein the Wnt inhibitor is used at a final concentration of 0.01-1200 ng/ml.

13. A method for inducing stem cell differentiation into a ventricular cardiomyocyte, comprising:
differentiating a stem cell to a mesodermal cell or a cardiac progenitor cell;
activating the Smad1/5/8 signaling pathway in the mesodermal cell or cardiac progenitor cell; and
inhibiting the Wnt signaling pathway in the mesodermal cell or cardiac progenitor cell, and
without purification, obtaining a cardiomyocyte cell population differentiated from the mesodermal cell or cardiac progenitor cell in which at least 80% of the cardiomyocyte population are ventricular cardiomyocytes,
wherein said mesodermal cell or cardiac progenitor cell is simultaneously contacted with an exogenous activator of the Smad1/5/8 signaling pathway and an exogenous inhibitor of the Wnt signaling pathway in a same cell culture medium, thereby activating said Smad1/5/8 signaling pathway and inhibiting said Wnt signaling pathway in said mesodermal cell or cardiac progenitor cell.

14. The method of claim 13, wherein the stem cell is differentiated to the mesodermal cell or cardiac progenitor cell by adding one or more factors that promote differentiation to cardiomyocyte in a culture medium of the stem cell.

15. The method of claim 14, wherein the one or more factors that promote differentiation to cardiomyocyte comprise at least one of BMP4, bFGF, Activin A, Noggin, Dorsomorphin, and a Wnt3a pathway activator.

16. The method of claim 13, wherein the Wnt signaling pathway is inhibited by adding an inhibitor of the Wnt signaling pathway in a culture medium of the mesodermal cell or cardia progenitor cell.

17. The method of claim 16, wherein the inhibitor of the Wnt signaling pathway comprises at least one of dickkopf homolog 1 (DKK1), IWP, and an inhibitor of Wnt response (IWR).

18. The method of claim 13, wherein the Smad1/5/8 signaling pathway is activated by adding in a culture medium of the mesodermal cell or cardia progenitor cell:
i) a BMP family member;
ii) an activator of retinoic acid receptor (RARγ), wherein the culture medium does not contain retinoic acid or a precursor thereof; or
iii) an antagonist of RARα and/or RARβ, wherein the culture medium contains retinoic acid or a precursor thereof.

19. The method of claim 18, wherein the BMP family member comprises BMP 2 and/or BMP 4.

20. A method for generating a ventricular cardiomyocyte from a stem cell, which method comprises:
1) contacting a stem cell with an agent to initiate stem cell differentiation;
2) differentiating the stem cell treated by the agent to form a mesodermal cell;
3) activating the Smad1/5/8 pathway in the mesodermal cell to promote ventricular cardiomyocyte formation;
4) contacting the mesodermal cell with one or more of DKK1, IWP, and an inhibitor of Wnt response (IWR) to differentiate the mesodermal cell into a ventricular cardiomyocyte; and
5) without purification, obtaining a cardiomyocyte cell population differentiated from the stem cell, wherein at least 80% of the cardiomyocyte population are ventricular cardiomyocytes,
wherein said mesodermal cell or cardiac progenitor cell is simultaneously contacted with an exogenous activator of the Smad1/5/8 signaling pathway and an exogenous one or more of DKK1, IWP and an inhibitor of Wnt response (IWR) in a same cell culture medium, thereby activating said Smad1/5/8 signaling pathway and inhibiting said Wnt signaling pathway in said mesodermal cell or cardiac progenitor cell.

21. The method of claim 20, wherein the Smad1/5/8 signaling pathway is activated by:
(i) contacting the mesodermal cell with a BMP family member;
(ii) contacting the mesodermal cell with an agonist of RARγ, wherein the mesodermal cell is cultured in a medium that does not comprise retinoic acid or a precursor thereof; or
(iii) contacting the mesodermal cell with an antagonist of RARα and/or RARβ, wherein the mesodermal cell is cultured in a medium comprising retinoic acid or a precursor thereof.

22. The method of claim 21, wherein the BMP family member comprises BMP 2 and/or BMP 4.

23. The method of claim 1, wherein the exogenous activator of the Smad1/5/8 signaling pathway comprises a BMP family member and the exogenous inhibitor of the Wnt signaling pathway comprises DKK1, and the same cell culture medium comprises both DKK1 and the BMP family member.

\* \* \* \* \*